United States Patent
Goldstein et al.

(10) Patent No.: US 12,427,155 B2
(45) Date of Patent: Sep. 30, 2025

(54) TREATMENT FOR TAU-RELATED DISEASES

(71) Applicant: The Regents of the University of California, Oakland, CA (US)

(72) Inventors: Lawrence Goldstein, La Jolla, CA (US); Rik Van Der Kant, La Jolla, CA (US); Robert Rissman, La Jolla, CA (US); Vanessa Langness, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 207 days.

(21) Appl. No.: 17/086,913

(22) Filed: Nov. 2, 2020

(65) Prior Publication Data
US 2021/0137933 A1 May 13, 2021

Related U.S. Application Data

(60) Provisional application No. 62/928,590, filed on Oct. 31, 2019.

(51) Int. Cl.
*A61K 31/536* (2006.01)
*A61P 25/28* (2006.01)

(52) U.S. Cl.
CPC ............ *A61K 31/536* (2013.01); *A61P 25/28* (2018.01)

(58) Field of Classification Search
CPC .............................. A61K 31/536; A61P 25/28
See application file for complete search history.

(56) References Cited

PUBLICATIONS

Alzforum: Networking for a Cure, "Cholesteryl Esters Hobble Proteasomes, Increase p-Tau", available online: Feb. 7, 2019. (Year: 2019).*
Van Der Kant, R., et al., "Cholesterol Metabolism Is a Druggable Axis that Independently Regulates Tau and Amyloid-B in iPSC-Derived Alzheimer's Disease Neurons", Cell Stem Cell (2019), 24, pp. 363-375. (Year: 2019).*
Pikuleva, Irina, "Efavirenz for Patients with Alzheimer's Disease", Case Western Reserve University, https://clinicaltrials.gov/ct2/history/NCT03706885?A=1&B=1&C=merged#StudyPageTop, available online: Oct. 16, 2018. (Year: 2018).*
Mast, N., et al., "Cholesterol-metabolizing enzyme cytochrome P450 46A1 as a pharmacologic target for Alzheimer's disease", Neuropharmacology (2017), 123: pp. 465-476. (Year: 2017).*
Rademakers, R., M. Cruts and C. van Broeckhoven, "The Role of Tau (MAPT) in Frontotemporal Dementia and Related Tauopathies", Human Mutation (2004), 24: pp. 277-295. (Year: 2004).*
Iqbal, K., F. Liu, C. Gong, A. Alonso, and I. Grundke-Iqbal, "Mechanisms of tau-induced neurodegeneration", Acta Neuropathol. (2009), 18(1), pp. 53-69. (Year: 2009).*
Wikipedia contributors, "Human body weight," Wikipedia, The Free Encyclopedia, https://en.wikipedia.org/w/index.php?title=Human_body_weight&oldid=1234444005 (accessed Aug. 17, 2024). (Year: 2024).*

* cited by examiner

*Primary Examiner* — Joseph K McKane
*Assistant Examiner* — Sagar Patel
(74) *Attorney, Agent, or Firm* — Eversheds-Sutherland (US) LLP

(57) ABSTRACT

Pharmaceutical compositions and methods for treatment of tauopathies, such as Alzheimer's disease and dementia, with low dosage efavirenz and derivatives.

4 Claims, 15 Drawing Sheets

TREATMENT FOR TAU-RELATED DISEASES

CROSS REFERENCE TO RELATED APPLICATIONS

This application claims the priority benefit of U.S. Provisional Application No. 62/928,590, filed Oct. 31, 2019, which application is incorporated herein by reference.

GOVERNMENT SPONSORSHIP

This invention was made with government support under grant AG048083 awarded by the National Institutes of Health. The government has certain rights in the invention.

TECHNICAL FIELD

The present invention relates to treatment for tauopathies, such as Alzheimer's disease and dementia.

BACKGROUND

Genetic, epidemiologic, and biochemical evidence suggests that predisposition to Alzheimer's disease (AD) may arise from altered cholesterol metabolism, although the molecular pathways that may link cholesterol to AD phenotypes are only partially understood.

Pathological accumulation of phosphorylated Tau (pTau) and accumulation of amyloid-beta (Aβ) fragments are the two major biochemical hallmarks of AD. Effective strategies to remove Aβ in AD-patient brains have been developed, but have not yet shown efficacy to slow cognitive decline in clinical trials. This finding has led to the idea that targeting Tau or combinatorial strategies that target both Tau and Aβ, are required to treat AD. While Aβ generation has been studied in much detail, the processes that drive pTau accumulation in AD are poorly defined. Late stage Tau pathology, such as aggregation of accumulated Tau in neurofibrillary tangles (NFT), and subsequent neurodegeneration can be modelled in mice, or non-neuronal human cells, by (over)expression of human mutant Tau.

However, Tau mutations do not occur in AD. Instead, in AD endogenous "wild-type" pTau accumulates downstream of FAD mutations (in APP, PSEN1 and PSEN2 genes) or, in the case of sporadic late-onset AD (SAD) downstream of an unknown combination of genetic and environmental risk factors. How these factors drive early accumulation of pTau in AD is not understood. Recent advances in induced pluripotent stem cell (iPSC) technology (Yanhong Shi et al., 2017) have made it possible to generate functional human neurons from patients and healthy controls to study early pathophysiological regulation of endogenous Tau. In iPSC-derived neurons from both FAD- and SAD-patients pTau aberrantly accumulates at early time points (Choi et al., 2014; Israel et al., 2012; Moore et al., 2015; Muratore et al., 2014; Ochalek et al., 2017; Yichen Shi et al., 2012). Accumulation of pTau in FAD neurons can be reversed by inhibition of β-secretase, the enzyme that converts APP to β-CTF indicating a direct relationship between APP processing and Tau (Israel et al., 2012; Moore et al., 2015). Interestingly, inhibition of γ-secretase (to prevent generation of Aβ from β-CTF) did not reduce pTau, indicating that the effect of APP processing on pTau in early AD neurons is not solely mediated by extracellular Aβ (Israel et al., 2012; Moore et al., 2015).

Identification of other cellular pathways that contribute to pTau accumulation early in familial AD (FAD) neurons, o, in the case of sporadic late-onset AD (SAD) neurons, is key to understanding Tau pathology in AD. In addition to increased Aβ and pTau levels, CE also accumulate in FAD and SAD. CE are increased in mouse models expressing human (mutant) APP (Chan et al., 2012; Tajima et al., 2013; Yang et al., 2014) and CE, as well as CE-storage organelles (lipid droplets), have been shown to accumulate in the SAD brain (Chan et al., 2012; Foley, 2010; Hamilton et al., 2015; Yang et al., 2014). CE are generated when cholesterol is converted to CE by the ER-resident Acyl-CoA cholesterol acyltransferase (ACAT) through ligation of a long-chain fatty acid to (excess) cholesterol, and CE can be converted back to cholesterol by acidic lipases in the lysosome (Ikonen, 2008; Puglielli et al., 2003). CE enhance the production of Aβ in vivo and in vitro indicating that CE can contribute to AD pathogenesis (Di Paolo and Kim, 2011; Hutter-Paier et al., 2004; Huttunen et al., 2009; Puglielli et al., 2003; 2001). CE-dependent regulation of Aβ generation is mediated by altered trafficking of APP through the early secretory pathway (Huttunen et al., 2009). Whether CE also affect Tau phosphorylation or Tau proteostasis is unknown, but inhibition of cholesterol esterification by genetic deletion of ACAT1 prevents early stage Tau pathology in Tau mutant mice through unknown mechanisms (Shibuya et al., 2015). A possible way by which CE could affect Tau pathology is through regulation of the ubiquitin-proteasome system (UPS). Cholesterol and cholesterol metabolites extensively interact with the UPS to regulate the ubiquitination and degradation of cholesterol-metabolic enzymes (Sharpe et al., 2014), and the UPS is a major regulator of pTau proteostasis. (M. J. Lee et al., 2013). Activity of the UPS is decreased in AD (Keck et al., 2003; Keller et al., 2001) and UPS (re)activation delays Tau aggregation and neurodegeneration in vitro and in vivo (Han et al., 2014; Lokireddy et al., 2015; Myeku et al., 2016).

SUMMARY OF THE INVENTION

The invention provides a method of treatment for tauopathy comprising administering to a subject in need thereof an effective amount of efavirenz or a derivative thereof. In embodiments, the effective amount is less than 50 mg per day, or about 0.01 mg to about 40 mg, or about 0.05 mg to 20 mg, or about 0.1 mg to 5 mg per day. In embodiments, the tauopathy causes neurofibrillary tangles. In embodiments, the tauopathy is Alzheimer's Disease. In embodiments, the tauopathy is fronto-temporal dementia.

The invention provides a method of reducing cholesteryl ester in a subject comprising administering to a subject in need an effective amount of efavirenz or a derivative thereof. In embodiments, the effective amount is less than 50 mg per day, or about 0.01 mg to about 40 mg, or about 0.05 mg to 20 mg, or about 0.1 mg to 5 mg per day. In embodiments, the cholesteryl ester is associated with tauopathy that causes neurofibrillary tangles. In embodiments, the tauopathy is Alzheimer's Disease. In embodiments, the tauopathy is fronto-temporal dementia.

BRIEF DESCRIPTION OF THE DRAWINGS

FIG. 1A shows screening strategy overview: APP$^{dp}$1-6 NPC's were differentiated for 3 weeks, replated into 384 well plates, and after 2 weeks, treated with 5 μM of compound for 5 days; pThr231Tau/tTau ratio and cell viability was measured. FIG. 1B shows 1,684 compounds (in pink) were screened in duplicate for their effect on pThr231Tau/tTau ratio as expressed by Z score. 158 compounds that decreased pThr231/tTau by Z≤−2 were selected for confirmation. Vehicle alone controls (DMSO) are shown in black. FIG. 1C shows 42 confirmed non-toxic hits grouped by drug category. SER, selective estrogen reuptake (n=4). FIG. 1D shows dosage effects of different statins on pThr231Tau/tTau ratio in APP$^{dp}$1-6 (mean±SEM, n≥3). FIG. 1E shows APP$^{dp}$1-6 neurons were treated with vehicle (DMSO, upper row) or atorvastatin (10 µM, lower row) for 5 days and fixed and stained with anti-bodies for indicated antigens. NF—H, neurofilament H, axonal marker. The pThr231Tau antibody used is TG3, which detects a conformational epitope of pThr231Tau. Scale bar, 100 µm.

FIG. 2A shows an overview of the mevalonate pathway and inhibitors used in this study. FIG. 2B shows APP$^{dp}$1-6 neurons were treated with DMSO or atorvastatin (10 µM) for 5 days. For indicated conditions, mevalonate (MVA, 0.5 mM), mevalonate-5-phosphate (MVP, 0.5 mM), or mevalonate-5-pyrophosphate (MVA-5PP, 1 mM) was added to the media at a single dose at t=0 (mean±SEM, n≥3). FIG. 2C shows APPdp1-6 neurons were treated with inhibitors of specific steps in the mevalonate pathway; atorvastatin (10 mM), FTI-227 (10 µM), GGTI (10 µM), YM-53601 (20 µM), AY-9944 (10 µM), fatostatin (20 µM), 24-hydroxycholesterol (10 µM), T0901317 (10 µM), rosiglitazone (50 µM), GW501516 (10 µM), and efavirenz (10 µM). pThr231Tau/tTau levels were determined by ELISA (mean±SEM, n>3). FIGS. 2D-2F show APP$^{dp}$1-6 neurons were treated with atorvastatin (10 µM), AY-9944 (5 µM), T0901317 (10 µM), or efavirenz (10 µM) for 3 days and lipid analysis was performed to measure (FIG. 2D) free cholesterol (mean±SEM, n≥8), (FIG. 2E) total cholesterol (mean±SEM, n≥4), and (FIG. 2F) CE (mean±SEM, n≥8). FIG. 2G shows pThr231Tau/tTau levels after 5-day treatment of APP$^{dp}$1-6 neurons with avasimibe (10 µM) or K604 (25 µM) (mean±SEM, n≥3). FIG. 2H shows treatment of APP$^{dp}$1-6 neurons with LDL (25 µg/mL) (mean±SEM, n≥3).

FIG. 3A shows dosage effect of simvastatin treatment on pThr231Tau/tTau on non-demented control (NDC) neurons (CV 151 line). FIGS. 3B-3C show effect of simvastatin (10 µM) (B) or efavirenz (10 µM) treatment (FIG. 3C) on pThr231Tau/tTau in neuronal lines from SAD and NDC subjects (mean±SEM, number of individual patients indicated in bars). FIG. 3D shows secreted Ab levels from APP$^{dp}$1-6 neurons treated with atorvastatin (10 µM) for 5 days normalized to DMSO-treated neurons (mean±SEM, n≥3). FIG. 3E shows the correlation of Ab42 and pThr231Tau/tTau levels in atorvastatin-treated neurons at different time points, dosages, and in different cell lines (light circles, APP$^{dp}$1-6; dark circles, APP$^{dp}$2-1). CC, correlation coefficient. FIGS. 3F-3G show characterization of APP$^{null}$ line. FIG. 3F shows western blot with antibodies against APP in isogenic APP$^{dp}$ (line APP$^{dp}$2-1) and APP$^{null}$ (line APP$^{dp}$1KO). Full-length APP (FL) and APP CTF are no longer detected in the APP$^{dp}$1$^{null}$ line. The FL-APP (22C11) cross reacts with APLP2 explaining the remaining signal in the FL-APP (22C11 blot). FIG. 3G shows ELISA analysis shows an absence of Aβ40 and Aβ42 in conditioned media from the APP$^{null}$ line. Positive control is APP$^{dp}$1-2, negative control is unconditioned media. The detection antibody for the ELISA is 6E10, as indicated in (FIG. 3F). FIG. 3H shows dosage effect of simvastatin treatment on pThr231Tau/tTau on neurons with indicated genotypes (mean±SEM, n≥3). Isogenic knockouts used were in an APP$^{dp}$ patient genetic back-ground (lines APP$^{dp}$1-2 [$^{dp}$] and APP$^{dp}$1KO [$^{null}$] or non-demented control [NDC] genetic background [CV line 151 (wild-type [WT])] and IB6 [$^{null}$]). Mean±SEM; n≥5.

FIG. 4A shows a schematic representation of the transmembrane domain of APP with amino acids essential for cholesterol binding indicated in yellow. FIG. 4B shows a schematic overview of the gene-editing strategy to generate APP-Δcholesterol lines. Green indicates amino acid sequence. Red arrow indicates CRISPR/Cas9 cut site. FIG. 4C shows sequencing results verifying correct incorporation of desired mutations in the APP-Δcholesterol lines. Two E693A (line 3D9 and 2B2) and one F691A+E693A line (line D12) were generated, as well as two non-gene-edited, but clonally expanded, WT lines (B10 and B11). FIGS. 4D-4F show measurements made using APP-Δcholesterol neurons with the following genotypes: WT (average from 2 independent lines), E693A (2 independent lines), and F691A+E693A (1 line) (mean±SEM, n R 3 per line). (D) Relative secreted Aβ levels in conditioned media from purified CD184⁻, CD44⁻, and CD24⁺ neurons (mean±SEM, n≥3 per line). FIG. 4E shows relative secreted Aβ42 in response to atorvastatin treatment (10 µM, 3 days) (mean±SEM, n≥3 per line) (FIG. 4F) pThr231Tau/tTau in response to atorvastatin treatment (10 µM, 3 days) in APP-Δcholesterol neurons (mean±SEM, n≥3 per line).

FIGS. 5A-5B show the effect of CE lowering treatments on Tau levels and Tau phosphorylation as assessed by western blot (FIG. 5A), quantified in (FIG. 5B) (mean±SEM, n≥3). Image is a composite of different loading positions on same blot, stitch is indicated by vertical line. FIG. 5C shows pThr231Tau/tTau levels in APP$^{dp}$1-6 neurons co-treated with atorvastatin (10 µm) and a lysosomal inhibitor (chloroquine, CQ 25 µM), a phosphatase inhibitor (okadaic acid, 1.25 nM) or a proteasome inhibitor (MG132, 5 µM) for 3 days as measured by ELISA (mean±SEM, n≥3). FIGS. 5D-5E show APP$^{dp}$1-6 neurons were treated for 3 days with DMSO, simvastatin (10 µM) or atorvastatin (10 µM) and levels of proteasome subunits PSMC2 and PSMb1/5 were assessed by western blot (FIG. 5D). Quantified in (FIG. 5E) (mean±SEM n≥3). PSMb1/5/actin image is a composite of different loading positions on same blot, stiches are indicated by vertical line. FIGS. 5F-5I show APP$^{dp}$1-6 (FIG. 5F and FIG. 5G) or NDC CV4a (FIG. 5H and FIG. 5I) neurons were treated for 3 days with DMSO, simvastatin (10 µM), atorvastatin (10 µM), or efavirenz (10 µM) and incubated with a proteasome activity binding probe (ABP) for 1 h. Cells were lysed, run on SDS-page, and ABP fluorescence from the gel was determined (mean±SEM, n≥5). FIG. 5G shows quantification of the western blots from FIG. 5F. FIG. 5I shows quantification of western blots from FIG. 5H. Images are composite of different loading positions on same blot, stiches are indicated by vertical lines.

FIG. 6A shows iPSC-derived astrocytes were fixed and stained with indicated antibodies. Scale bar, 10 µm. FIGS. 6B-6D show iPSC-derived APP$^{dp}$1-6 astrocytes were treated for 3 days with increasing concentrations of (FIG. 6B) atorvastatin, (FIG. 6C) simvastatin, and (FIG. 6D)

efavirenz, and viability was measured (cell titer glo). Astrocytic viability (blue line) was plotted against results from FIGS. 1D and S1A for statins (neuronal viability and pThr231Tau/Tau ratio). For efavirenz, dose responses to measure pThr231Tau/tTau and neuronal viability were performed in APP$^{dp}$1-6 neurons (mean±SEM, n≥3-6). FIG. 6E shows a model depicting the relationship between CE, pTau, and Aβ in early AD neurons. Statins reduce CE levels through inhibition of the cholesterol-synthetic pathway, while efavirenz enhances the turnover of cholesterol to 24-hydroxycholesterol that causes conversion of CE to cholesterol and a reduction in CE. Reduced CE cause proteasomal upregulation and degradation of pTau. In a correlated, but independent pathway, CE regulate APP processing and Aβ generation.

(FIG. 7A) Representative sections stained for PHF-1. Low power images show areas of enlargements where measurements were obtained. (FIGS. 7B-7D) Sections were analyzed with video bright field microscopy and immunoreactivity was quantified as corrected optical density. * indicated p<0.05 compared to vehicle treated 4RTau-tg mice, ** indicates p<0.005 compared to vehicle treated 4RTau-tg mice. Scale bar=200 μm in low power images and 20 μm in higher power images.

(FIG. 8A) Representative sections stained for GFAP. Low power images show areas of enlargements where measurements were obtained. (FIGS. 8B-8C) Sections were analyzed with video bright field microscopy and immunoreactivity was quantified as % area of neuropil. Scale bar=100 μm in low power images and 20 μm in higher power images.

(FIG. 9A) Representative sections stained for SY38 (red) and mounted with DAPI (blue). Low power images show areas of enlargements where measurements were obtained. (FIGS. 9B-9D) Sections were analyzed with fluorescence microscopy and immunoreactivity was quantified as corrected optical density. Scale bar=50 μm.

DETAILED DESCRIPTION

Figure 1A:
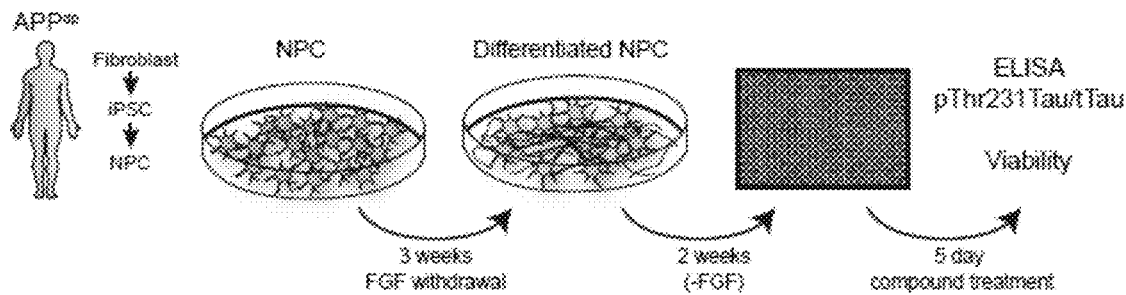
FIGS. 1A-1E show identification of Compounds that Decrease pTau Levels in FAD iPSC-Derived AD Neurons.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, $20^{th}$ ed., (Lippincott, Williams & Wilkins 2003), and Remington, The Science and Practice of Pharmacy, $22^{nd}$ ed., (Pharmaceutical Press and Philadelphia College of Pharmacy at University of the Sciences 2012).

The invention provides a method of treatment for tauopathy comprising administering to a subject in need thereof an effective amount of efavirenz or a derivative thereof, including salts thereof and precursors and metabolites thereof. In embodiments, the effective amount is less than 50 mg per day. In embodiments, the effective amount is about 0.01 mg to about 40 mg, or about 0.05 mg to 20 mg, or about 0.1 mg to 5 mg per day.

The invention provides a method of reducing an amount of cholesteryl ester in a subject comprising administering to a subject in need an effective amount of efavirenz or a derivative thereof. In embodiments, the effective amount is less than 50 mg per day. In embodiments, the effective amount is about 0.01 mg to about 40 mg, or about 0.05 mg to 20 mg, or about 0.1 mg to 5 mg per day.

In embodiments, the subject is a mammal. In embodiments, the subject is a human. In embodiments, the tauopathy causes neurofibrillary tangles. In embodiments, the tauopathy is Alzheimer's Disease. In embodiments, the tauopathy is fronto-temporal dementia. In embodiments, the tauopathy is selected from primary age-related tauopathy (PART)/Neurofibrillary tangle-predominant senile dementia, with NFTs similar to AD, but without plaques, chronic traumatic encephalopathy (CTE), progressive supranuclear palsy (PSP), corticobasal degeneration (CBD), frontotemporal dementia and parkinsonism linked to chromosome 17 (FTDP-17), Lytico-bodig disease (Parkinson-dementia complex of Guam), ganglioglioma and gangliocytoma, meningioangiomatosis, postencephalitic parkinsonism, subacute sclerosing panencephalitis (SSPE), lead encephalopathy, tuberous sclerosis, pantothenate kinase-associated neurodegeneration, and lipofuscinosis.

The invention provides a pharmaceutical composition comprising an effective amount of efavirenz or a derivative thereof to treat a tauopathy in a mammalian subject, and a pharmaceutically acceptable carrier. In embodiments, the effective amount is less than 50 mg per day. In embodiments, the effective amount is about 0.01 mg to about 40 mg, or about 0.05 mg to 20 mg, or about 0.1 mg to 5 mg per day. In embodiments, the tauopathy causes neurofibrillary tangles. In embodiments, the tauopathy is Alzheimer's Disease. In embodiments, the tauopathy is fronto-temporal dementia.

Efavirenz is chemically described as (S)-6-chloro-(cyclopropylethynyl)-1,4-dihydro-4-(trifluoromethyl)-2H-3,1-benzoxazin-2-one. Its empirical formula is $C_{14}H_9ClF_3NO_2$.

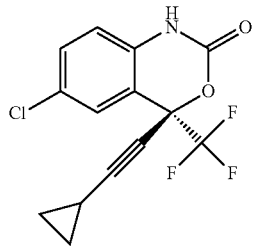 [SMILES: O=C1Nc2ccc(Cl)cc2[C@@](C#CC2CC2)(C(F)(F)F)O1]

The invention contemplates alternative methods and compositions for reducing an amount of cholesteryl ester (CE) to treat a Tau-related disease in a subject comprising administering to a subject in need an effective amount of a CE production inhibiting compound. For example, inhibiting CE production can be achieved by inhibiting Acyl-CoA cholesterol acyltransferase (ACAT) ability to convert cholesterol to CE.

As used herein, the terms "comprises," "comprising," "includes," "including," "has," "having," "contains", "containing," "characterized by," or any other variation thereof, are intended to encompass a non-exclusive inclusion, subject to any limitation explicitly indicated otherwise, of the recited components. For example, a pharmaceutical composition, and/or a method that "comprises" a list of elements (e.g., components, features, or steps), is not necessarily limited to only those elements (or components or steps), but may include other elements (or components or steps) not expressly listed or inherent to the pharmaceutical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a fusion protein, pharmaceutical composition, and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein the term "pharmaceutical composition" refers to a pharmaceutical acceptable compositions, wherein the composition comprises a pharmaceutically active agent, and in some embodiments further comprises a pharmaceutically acceptable carrier. In some embodiments, the pharmaceutical composition may be a combination of pharmaceutically active agents and carriers.

The term "combination" refers to either a fixed combination in one dosage unit form, or a kit of parts for the combined administration where one or more active compounds and a combination partner (e.g., another drug as explained below, also referred to as "therapeutic agent" or "co-agent") may be administered independently at the same time or separately within time intervals. In some circumstances, the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "therapeutically effective" refers to an amount of a pharmaceutically active compound(s) that is sufficient to treat or ameliorate, or in some manner reduce the symptoms associated with diseases and medical conditions. When used with reference to a method, the method is sufficiently effective to treat or ameliorate, or in some manner reduce the symptoms associated with diseases or conditions. For example, an effective amount in reference to diseases is that amount which is sufficient to block or prevent onset; or if disease pathology has begun, to palliate, ameliorate, stabilize, reverse or slow progression of the disease, or otherwise reduce pathological consequences of the disease. In any case, an effective amount may be given in single or divided doses.

As used herein, the terms "treat," "treatment," or "treating" embraces at least an amelioration of the symptoms associated with diseases in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice, and the like. In specific embodiments, the subject is a human. The terms "subject" and "patient" are used interchangeably herein in reference, for example, to a mammalian subject, such as a human.

The term "derivative" refers to a chemical substance related structurally to another substance, or a chemical substance that can be made from another substance (i.e., the substance it is derived from), e.g., through chemical or enzymatic modification, which is pharmaceutically active and therapeutically effective for the methods described herein.

As used herein, and unless otherwise specified, a compound described herein is intended to encompass all possible stereoisomers, unless a particular stereochemistry is specified. Where structural isomers of a compound are interconvertible via a low energy barrier, the compound may exist as a single tautomer or a mixture of tautomers. This can take the form of proton tautomerism; or so-called valence tautomerism in the compound, e.g., that contain an aromatic moiety.

The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent agent or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of an agent or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. An agent or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

The term "pharmaceutically acceptable carrier" as used herein refers to an excipient, diluent, preservative, solubilizer, emulsifier, adjuvant, and/or vehicle with which an agent or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20'" ed., (Lippincott, Williams & Wilkins 2003). Except insofar as any conventional media or agent is incompatible with the active compound, such use in the compositions is contemplated.

As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as a hemolytic disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

These and other features and aspects of the present invention will be apparent to one skilled in the art in view of the particular embodiments disclosed herein, which are not to be construed as limiting the scope of the invention.

EXAMPLES

This example provides a phenotypic screen for pTau accumulation in AD-patient iPSC-derived neurons and identifies cholesteryl esters (CE), the storage product of excess cholesterol, as upstream regulators of Tau early during AD development. Using isogenic induced pluripotent stem cell (iPSC) lines carrying mutations in the cholesterol-binding domain of APP or APP null alleles, it was determined that while CE also regulate Ab secretion, the effects of CE on Tau and Aβ are mediated by independent pathways. Efficacy and toxicity screening in iPSC-derived astrocytes and neurons showed that allosteric activation of CYP46A1 lowers CE specifically in neurons and is well tolerated by astrocytes. These data reveal that CE independently regulate Tau and Aβ and identify a druggable CYP46A1-CE-Tau axis in AD.

Figure 1B:
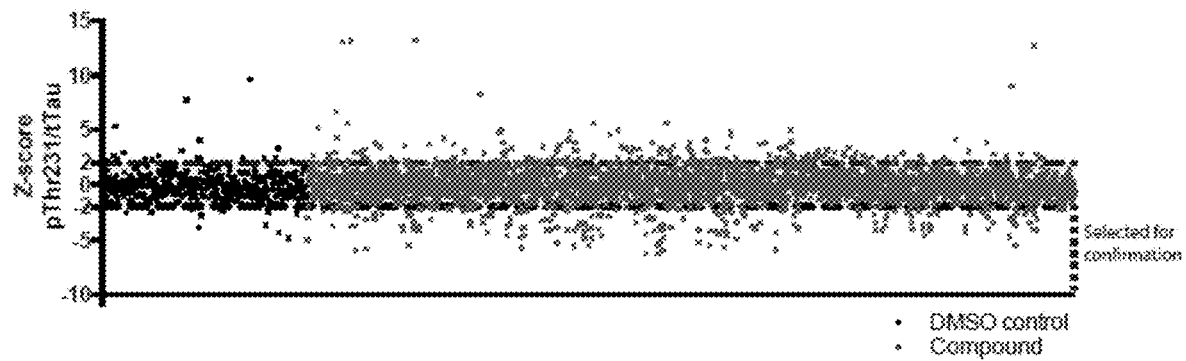

A Drug Screen in iPSC-Derived Human FAD Neurons to Identify Compounds that Reduce pTau Accumulation pThr231Tau is an early marker of AD pathology that correlates well with cognitive decline (Buerger et al., 2002; Luna-Muñoz et al., 2007). pThr231Tau accumulates in APP duplication ($APP^{dp}$) iPSC-derived FAD neurons (Israel et al., 2012). To identify compounds that reduce pTau accumulation in these FAD neurons, a collection of 1684 approved and preclinical drugs were screened for their efficacy to lower neuronal pThr231Tau. For the screen, neural progenitor cells (NPCs; line $APP^{dp}$1-6 (Israel et al., 2012) were differentiated to neurons for three weeks, replated in 384 well plates and allowed to mature for two weeks before treatment with compound at 5 µM for five days. The screen was performed in duplicate and a ratiometric read-out of pThr231Tau/total Tau (tTau) level and cell viability, was determined (FIG. 1a). In the primary screen 158/1684 compounds (9.4%) significantly reduced pThr231/tTau by a Z-score<−2 in at least one of the duplicates (FIG. 1b) and were selected for confirmation.

Figure 1C:
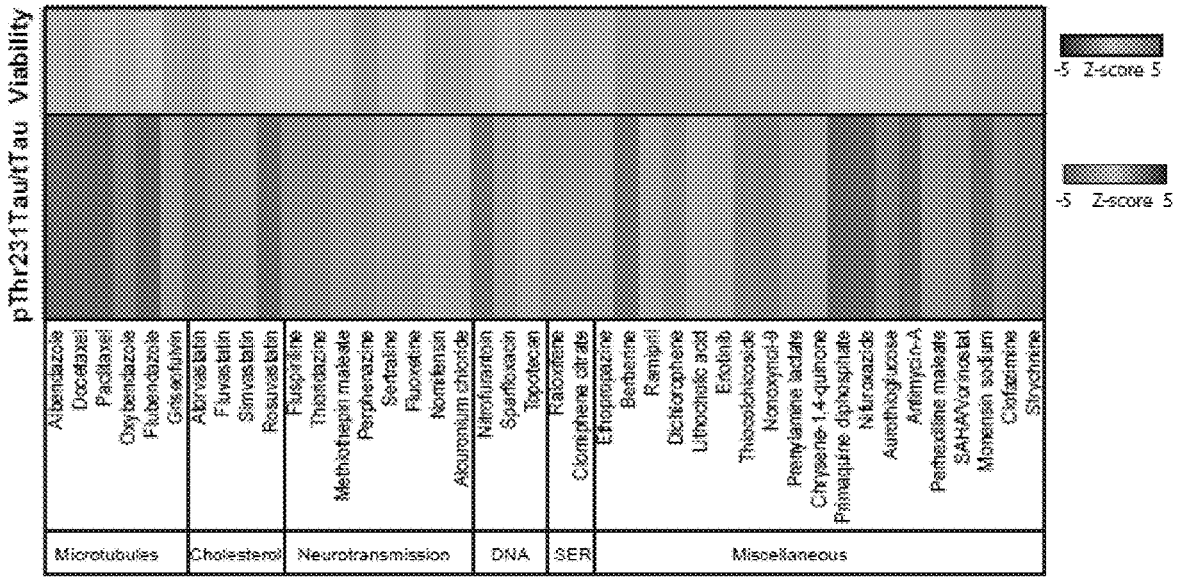

In a repeat of the primary assay with selected compounds 96/158 compounds confirmed in at least one additional replicate. Of the 96 confirmed compounds, 42 were clearly non-toxic hits with Z>−1 for viability (FIG. 1c). This screen identified six microtubule-interacting compounds that reduced pThr231Tau/tTau (14% of hits) that have previously been shown to regulate pTau in other systems (Dickey et al., 2006; Merrick et al., 1996; Xie et al., 1998). The hit-list also included four inhibitors of cholesterol synthesis; atorvastatin, simvastatin, fluvastatin and rosuvastatin. Since cholesterol metabolism has been heavily linked to AD pathogenesis (Di Paolo and Kim, 2011), these compounds were selected for further study.

Figure 1D:
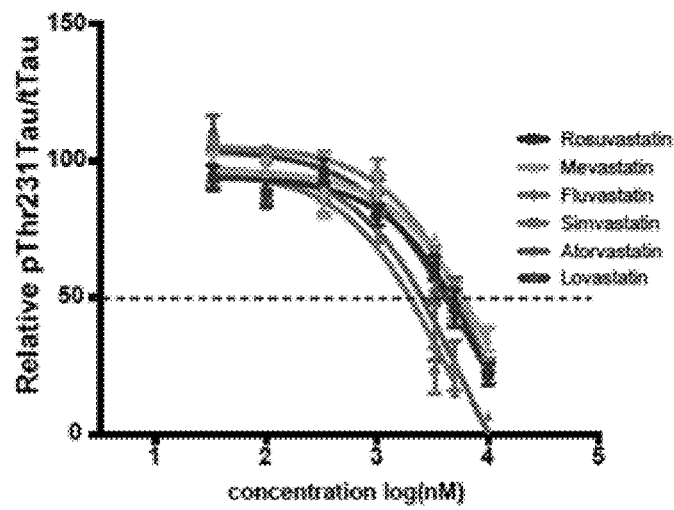
Figure 1E:
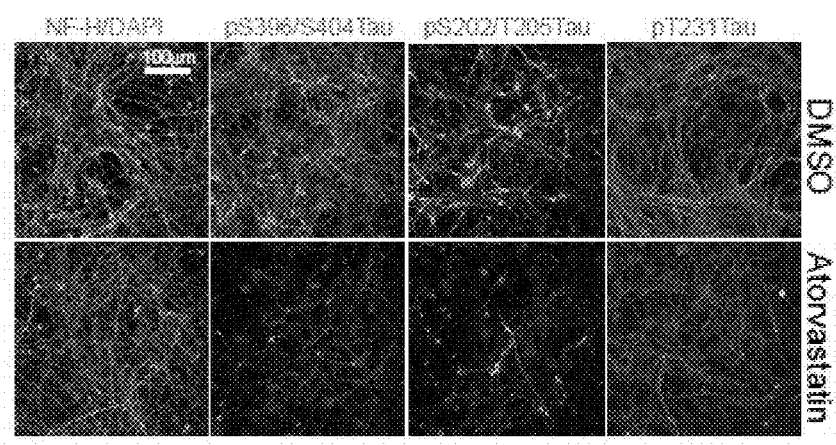

The research confirmed that these four statins, as well as two additional statins (lovastatin, mevastatin), reduced pThr231Tau/tTau in a dose-dependent manner with minor effects on cell viability or neuronal number (FIG. 1d). Simvastatin reduced pThr231Tau in a similar dose-dependent manner in additional lines from the same patient (APP$^{dp}$1-2) and an independent patient APP$^{dp}$ line (1) (APP$^{dp}$2-1), indicating that the effect of statins is conserved across individual APP$^{dp}$ lines and patients. In addition to pThr231Tau/tTau, atorvastatin also reduced pS396/S404Tau, pS202/T205Tau and levels of a pThr231 phosphorylation-dependent conformational Tau epitope (TG3) as assessed by immunofluorescence (FIG. 1e). These data show that in addition to screening for Aβ (Brownjohn et al., 2017; Kondo et al., 2017), iPSC-derived AD neurons can be applied to screen for pTau modulators. In addition, these data show that statins reduce pTau levels across a number of phosphorylation epitopes and across individual FAD (APP$^{dp}$) patients.

The Effect of Statins on pTau is Mediated by Cholesteryl Esters

Figures 2A, 2B, 2C, 2D, 2E, 2F, 2G, 2H:
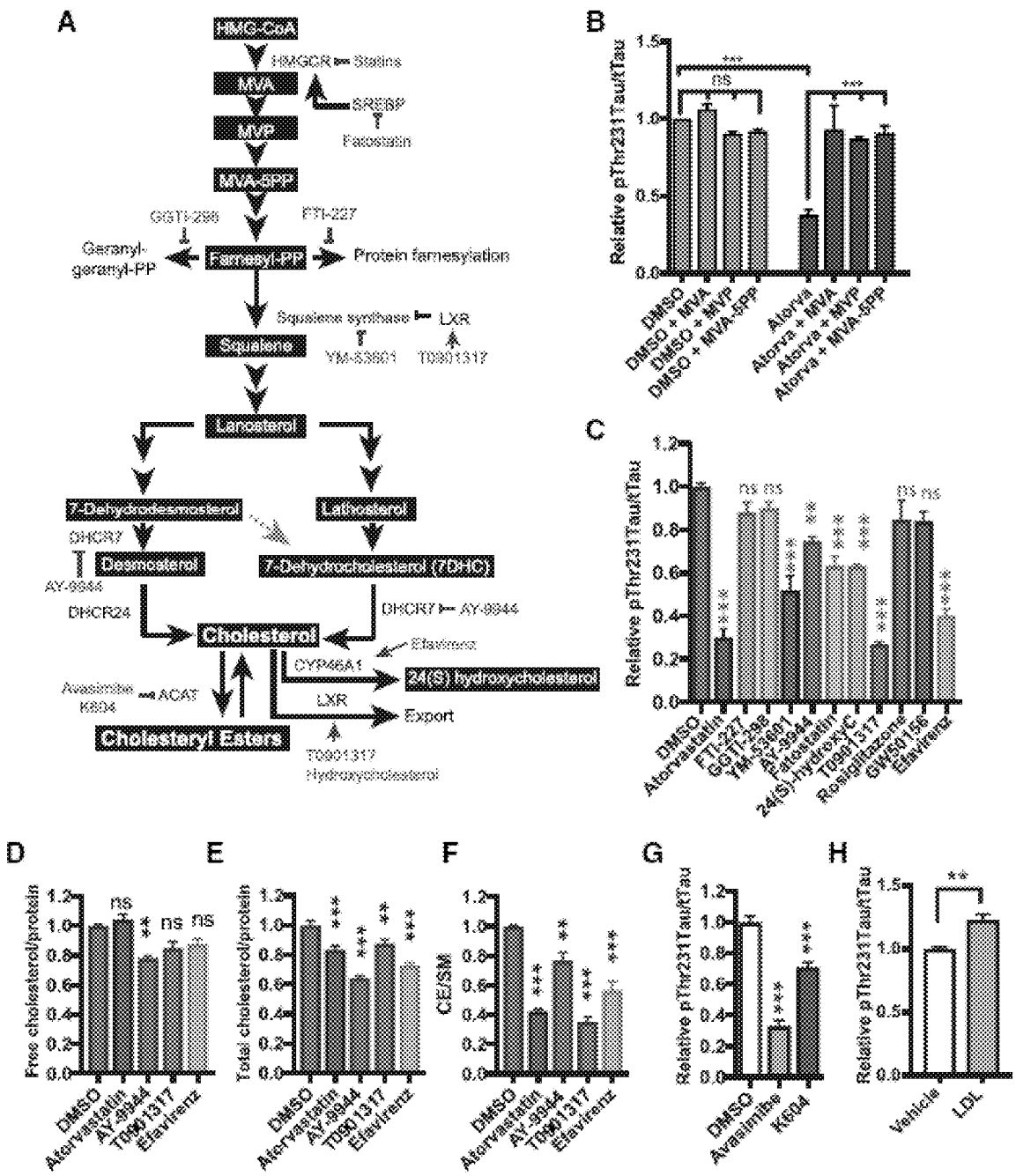
FIGS. 2A-2H show the Effect of Statins on pTau Is Mediated by Cholesteryl Esters.

To understand how pTau is regulated by statins, the relationship between the mevalonate-cholesterol synthetic pathway and pTau levels was studied in more detail. Statins inhibit 3-Hydroxy-3-Methylglutaryl-CoA Reductase (HMGCR), an early rate limiting step in the cholesterol synthetic pathway that converts HMG-CoA to mevalonate (MVA) (FIG. 2a). As expected, MVA supplementation rescued the effect of atorvastatin treatment on pThr231Tau/tTau indicating that the effect of statins on pTau is specific to their effects on the mevalonate pathway (FIG. 2b). While atorvastatin was slightly cytotoxic at higher concentrations toxicity did not explain the effect of atorvastatin on pThr231Tau/tTau, as MVA supplementation completely rescued the effect of atorvastatin on pThr231Tau/tTau ratio without rescuing the minor effect of atorvastatin on cell viability. Removal of atorvastatin after five days of treatment allowed recovery of pThr231Tau/Tau indicating reversible dynamic regulation. Statin treated neurons elicited a (normal) physiological response to statin treatment exemplified by upregulation of cholesterol-synthetic proteins. Statins have recently been reported to induce the degradation of mutant p53 by reduction of mevalonate-5-phosphate (MVP) (Parrales et al., 2016). The effects of statins on pTau are not mediated by MVP, as both MVP and its direct downstream metabolite MVA-5PP rescued the effect of statin treatment (FIG. 2b). More distal of MVA-5PP, the MVA pathway branches into non-sterol isoprenoid (protein prenylation) pathways and a cholesterol synthetic pathway (FIG. 2a). Inhibition of the respective non-sterol isoprenoid pathways (by geranyl- or farnesyl-transferase inhibitors GGTI-298 and FTI-227 respectively) did not significantly reduce pThr231Tau/tTau (FIG. 2c). In contrast, inhibition of the cholesterol-synthetic arm of the mevalonate pathway using a squalene synthase inhibitor (YM-53601) or Δ7-dehydrocholesterol reductase (DHCR7) inhibitor (AY-9944) did significantly decrease pThr231Tau/tTau (FIG. 2c), indicating that pTau is regulated by the cholesterol-synthetic branch of the MVA pathway. Alternative ways to reduce neuronal cholesterol such as inhibition of sterol regulatory element-binding protein (SREBP)-mediated transcriptional activation of cholesterol synthetic genes by fatostatin (Kamisuki et al., 2009) (FIG. 2c) or induction of cholesterol export by Liver X Receptor (LXR) agonists (FIG. 2a) T091317 and 24-hydroxycholesterol (FIG. 2c) also reduced pThr231Tau/tTau. Activation of homologous nuclear receptors such as PPARα (by GW50156) and PPARγ (by Rosiglitazone), which regulate fatty acid metabolism but not cholesterol export, did not decrease pThr231Tau/tTau (FIG. 2c).

Another strategy to reduce the pool of neuronal cholesterol is the activation of cholesterol 24-hydroxylase (CYP46A1), a neuron specific enzyme that converts cholesterol to 24-hydroxycholesterol (Anderson et al., 2016; Mast et al., 2017b; Moutinho et al., 2016). As expected, activation of CYP46A1 by efavirenz (FIG. 2c) or overexpression of CYP46A1 also reduced pThr231Tau/tTau. Together these data show that mechanistically different cholesterol-lowering drugs all reduce pTau, strongly indicating that pTau levels are controlled by neuronal cholesterol levels or downstream cholesterol metabolites. To determine whether cholesterol itself or a cholesterol metabolite controls pTau levels, extensive lipid analysis was performed for key selected compounds from previous experiments (FIG. 2d-f). None of the pTau-reducing drugs affected phospholipid levels (sphingomyelin (SM) and phosphatidylanolamine (PE). Cholesterol precursor levels were altered in accordance with the enzymatic target of the different compounds; atorvastatin reduced desmosterol levels and trended towards decreased 7DHC levels, AY9944 reduced desmosterol and increased 7DHC levels; T091317 decreased desmosterol levels (LXR is also a negative regulator of squalene synthase); and efavirenz only had a minor inhibitory effect on precursor levels. 24-hydroxycholesterol (a direct downstream metabolite of cholesterol) was increased in media from efavirenz treated neurons, was decreased in AY-9944 treated samples and unaltered in atorvastatin- and T091317 treated neurons. Surprisingly however, although these compounds behaved as expected, only AY-9944 (which only had minor effect on pTau, FIG. 2c) reduced free cholesterol levels (FIG. 2d).

It is important to note that these iPSC-derived neurons are cultured in media without an exogenous source of cholesterol, and thus neuronal cholesterol levels cannot be compensated by enhanced uptake from the media. Whereas changes in free cholesterol levels were not detected for most compounds, all compounds significantly reduced the levels of total cholesterol (free+esterified cholesterol) (FIG. 2e) through a strong reduction of CE (FIG. 2f). This finding suggests that conversion of CE to cholesterol compensates for the loss of cholesterol through inhibition of synthesis or induction of export, and that reductions in CE, not free cholesterol, mediate the effects of the different compounds on pTau. In line with this observation, direct inhibition of cholesterol esterification by the ACAT inhibitors avasimibe (aka CI-1011) (FIG. 2g) (Huttunen et al., 2009; 2010; H. T. Lee et al., 1996) or K604 (FIG. 2g) also reduced pTau. Exogenous addition of cholesterol/CE (in the form of LDL) increased pThr231Tau/tTau (FIG. 2h) levels. Together our data show that CE regulate pTau levels in human FAD neurons. The mechanisms underlying CE-dependent regulation of pTau were investigated in more detail.

Regulation of pTau by CE is Correlated with, but Independent of, APP and Aβ.

Figures 3A, 3B, 3C, 3D, 3E, 3F, 3G, 3H:
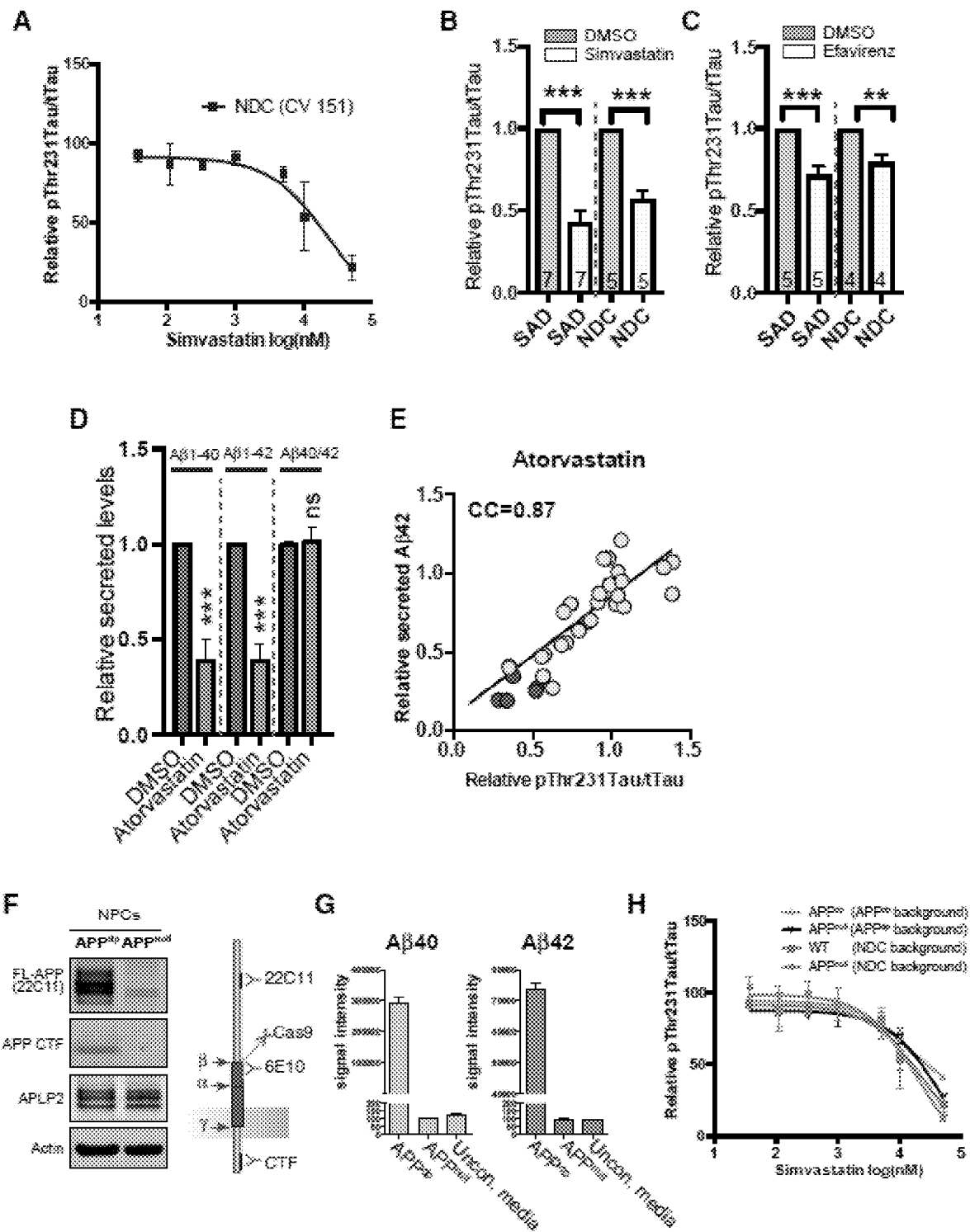
FIGS. 3A-3H shows pTau and Aβ Are Co-regulated by CE through Separate Pathways.

APP$^{dp}$ neurons have an extra copy of APP and increased levels of both Aβ and pTau (Israel et al., 2012; Moore et al., 2015). To understand the relationship between APP copy number, Aβ and CE-dependent regulation of pTau in more detail, NDC neurons were also treated with the normal two copies of APP with cholesterol-targeting drugs. Simvastatin, atorvastatin, efavirenz and the ACAT inhibitors avasimibe and K604 all reduced pThr231Tau/tTau also in the NDC neurons. For simvastatin, an extensive dose range was further tested, and found that it reduced pThr231Tau/Tau in NDC-neurons in a similar dose-dependent manner as in APP$^{dp}$ neurons (FIG. 3a). A single dose of statin or efavirenz also decreased pThr231Tau/tTau in sporadic Alzheimer's disease (SAD) patient- and non-demented control (NDC) neurons (FIG. 3b-c). pThr231Tau/tTau was also reduced by simvastatin in cultured hippocampal mouse neurons. Together, these data indicate that CE-dependent regulation of pTau is conserved across individual patients and healthy subjects (and even across species) and is not dependent on baseline APP copy number.

In addition to the findings on pTau, CE reduction has previously also been reported to reduce Aβ levels (Hutter-Paier et al., 2004; Huttunen et al., 2009; Puglielli et al., 2001) and Aβ secretion from iPSC derived neurons was also decreased by statins (FIG. 3d). A strong correlation between Aβ42 secretion and pThr231Tau/tTau was observed in response to atorvastatin treatment across time points and drug doses (FIG. 3e). To test whether the effect of CE on pTau was mediated by alterations in APP processing and/or the reduction of Aβ, an isogenic APP$^{null}$ line in an APP$^{dp}$ patient genetic background was generated (FIG. 3f-g). No APP expression or Aβ secretion was detected in the APP$^{null}$ neurons (FIG. 3f-g). pThr231Tau/tTau levels were reduced at baseline in the APP$^{null}$ neurons. Interestingly, in these APP$^{null}$ neurons, simvastatin still reduced pThr231Tau/tTau in a dose dependent manner identical to that of its isogenic control lines (FIG. 3h). Similarly, simvastatin reduced pThr231Tau/tTau the same in a previously generated isogenic set of NDC (APP$^{wt}$) and APP$^{null}$ neurons (CV line 151 and 1B6) (Fong et al., 2018) (FIG. 3h). Together these data show that CE regulate both pTau and Aβ, but that regulation of pTau by CE is APP and Aβ independent.

The Effect of CE on Aβ is Mediated by a Cholesterol-Binding Domain in APP.

Figures 4A, 4B, 4C, 4D, 4E, 4F:
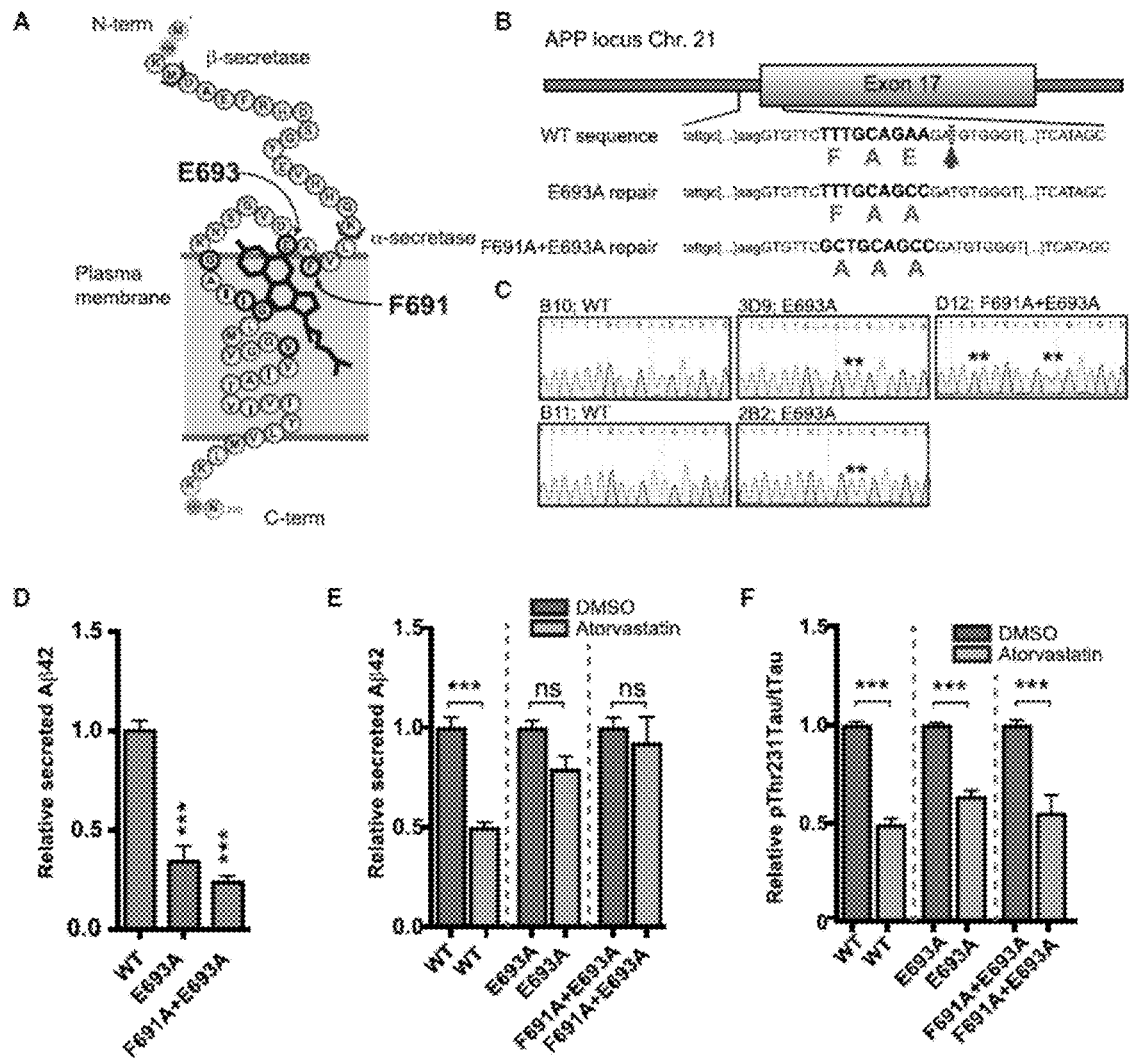
FIGS. 4A-4F show regulation of Aβ by CE Is Mediated by a Cholesterol Binding Domain in APP.

To understand the respective pathways by which CE regulate pTau and Aβ, and to verify that these pathways are indeed separate, the relationship between CE and Aβ secretion was first studied in more detail. It was hypothesized that the effect of CE on Aβ secretion could be mediated by a recently identified cholesterol-binding domain in APP β-CTF (Barrett et al., 2012). CRISPR/Cas9 was used to mutate the cholesterol-binding domain in the endogenous APP locus (FIG. 4a-c) and created two mutations that had previously been shown to abolish APP β-CTF-cholesterol interactions (Barrett et al., 2012); APP E693A and APP F691A+E693A. It was observed that Aβ42 secretion in these isogenic APP-Δcholesterol lines was reduced under steady state conditions (FIG. 4d) indicating that the cholesterol-binding domain affects APP processing and Aβ secretion. More importantly, atorvastatin treatment (FIG. 4e) did not affect Aβ42 secretion in these neurons indicating that the effect of lowering CE on Aβ42 is mediated by the cholesterol-binding domain in APP. While Aβ secretion was no longer regulated by atorvastatin in these neurons, atorvastatin still decreased pT231Tau/tTau ratio (in an identical manner as in their isogenic wild-type controls) (FIG. 4n, again confirming that the effect of CE on pTau and the effect of CE on Aβ are regulated through two separate pathways.

The Effect of CE on pTau Levels is Mediated by the Proteasome.

Figures 5A, 5B, 5C, 5D, 5E, 5F, 5G, 5H, 5I:
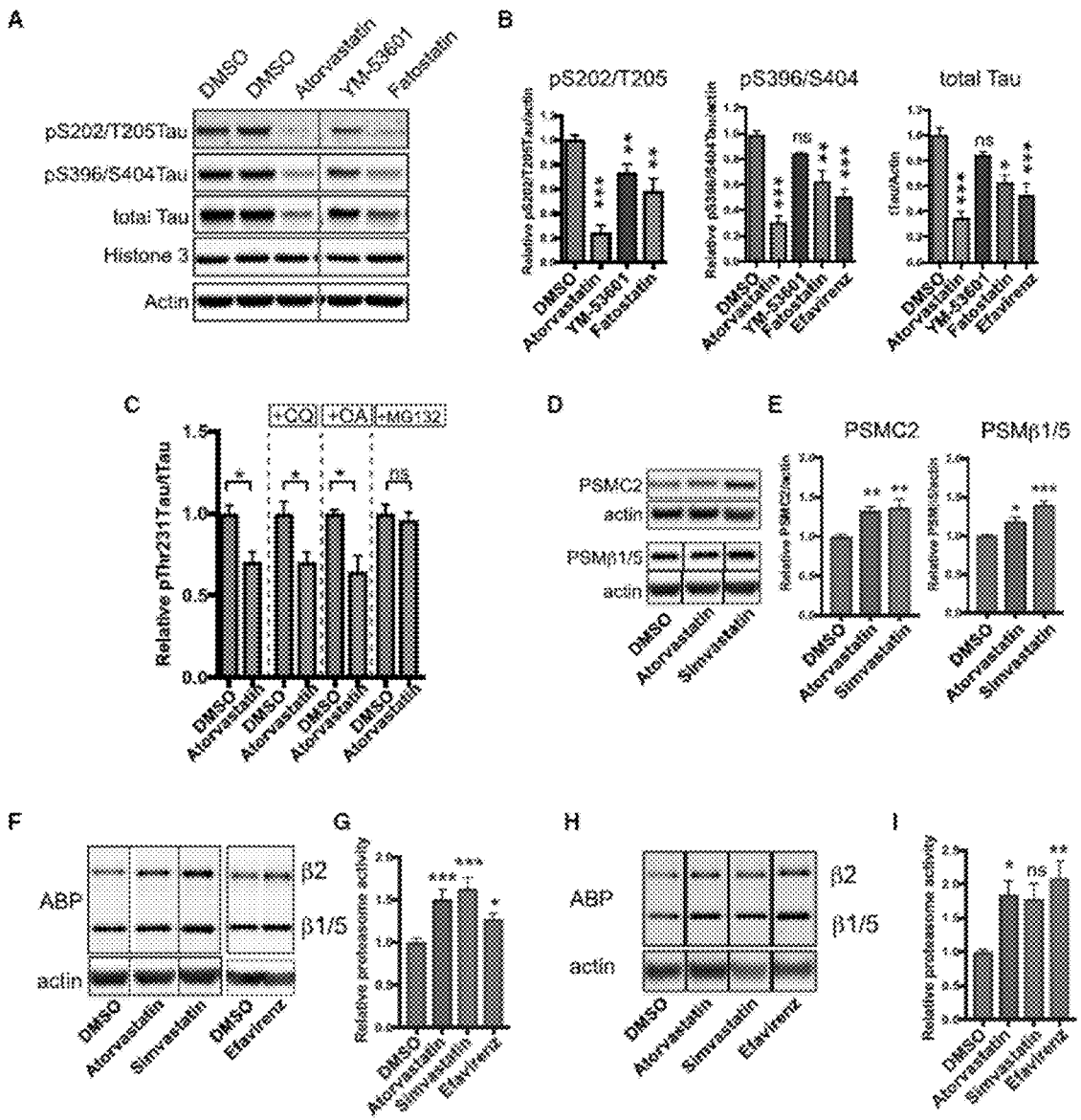
FIGS. 5A-5I show regulation of pTau by CE Is Mediated by the Proteasome.

Previous reports indicate that accumulation of pTau in FAD neurons can be downstream of altered proteostatic regulation of (p)Tau (Moore et al., 2015). To assess whether CE affect the proteostatic regulation of pTau by CE quantitative western blot was performed on APP$^{dp}$ neurons treated with different CE-targeting drugs. In addition to a reduction of pS396/S404Tau and pS202/T205Tau, CE reduction also reduced total Tau (FIG. 5a-b). The reduction of pTau and total Tau by these treatments was not explained by a specific loss of neurons in the cultures. The reduction of both pTau as well as tTau could indicate a proteostatic regulatory event, rather than altered Tau phosphorylation/dephosphorylation events. This was further substantiated by the finding that activity of GSK3β (a major Tau kinase) was not affected by statin-mediated CE reduction. Next, it was attempted to rescue the effect of CE reduction on pThr231Tau/tTau with inhibitors of phosphatase activity (okadaic acid), proteasomal—(MG132) or lysosomal/autophagosomal (chloroquine)—degradation (FIG. 5c). Only proteasomal inhibition abrogated the decrease in pThr231Tau/tTau ratio induced by atorvastatin (FIG. 5c, FIG. 5n), indicating that the effect of CE on pTau is mediated by the proteasome. Interestingly, in addition to cholesterol-synthetic genes, it was determined that the 26S proteasome regulatory subunit 7 (PSMC2) was also upregulated after statin treatment in NDC neurons. Western blot in APP$^{dp}$ neurons confirmed that statin treatment increased the levels of proteasomal subunit PSMC2 (FIG. 5d-e). Levels of another proteasome subunit, proteasome subunit beta type-5 (PSMβ5) in the core of the proteasome, were also increased (FIG. 5d-e). This statin dependent increase in proteasome levels is not mediated by transcriptional upregulation of proteasomal subunits. Using a proteasome activity binding probe (Berkers et al., 2007; Leestemaker et al., 2017) it was determined that CE-reduction through either statins or efavirenz increased total cellular proteasome activity in both APPdp and NDC neurons (FIG. 5f-i). The effect of CE on proteasome function was independent of mechanistic target of rapamycin (mTor). Together the data show that reducing neuronal CE enhances proteasome levels, total cellular proteasome activity and induces the proteasomal degradation of pTau indicative of a novel CE-proteasome-Tau axis.

CYP46A1 Activation is a Neuron Specific CE-Reducing Approach that is Better Tolerated by Astrocytes than HMGCR-Inhibitors (Statins).

Figure 6A:
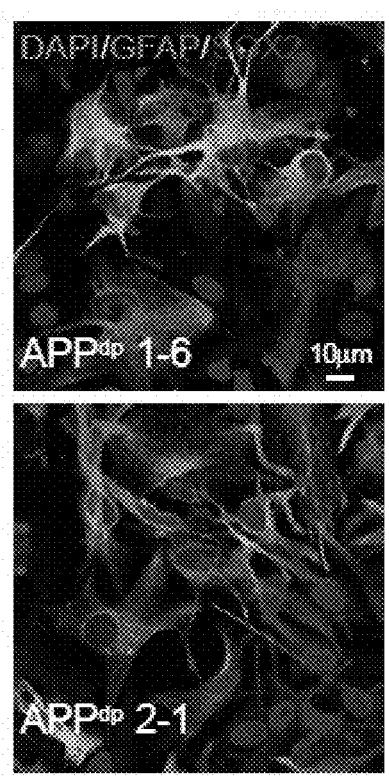
FIGS. 6A-6E show CYP46A1 activation is a neuron-specific CE-reducing approach that is better tolerated by astrocytes.
Figure 6B:
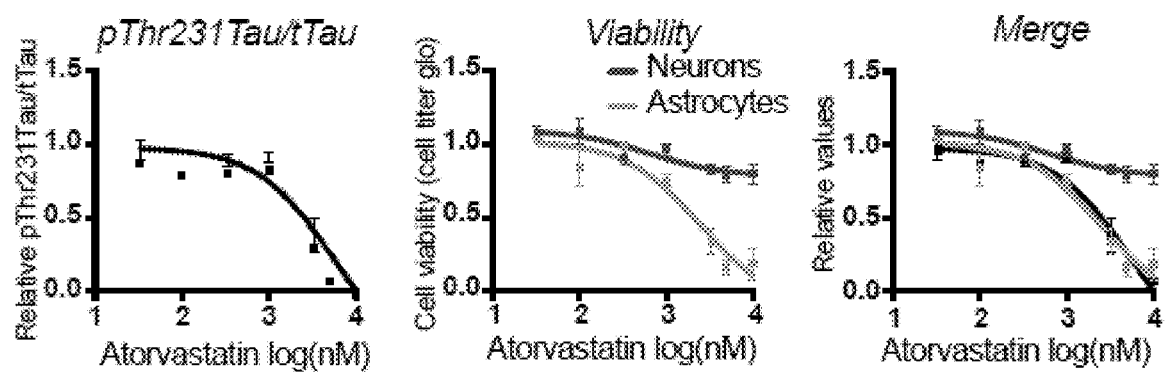
Figure 6C:
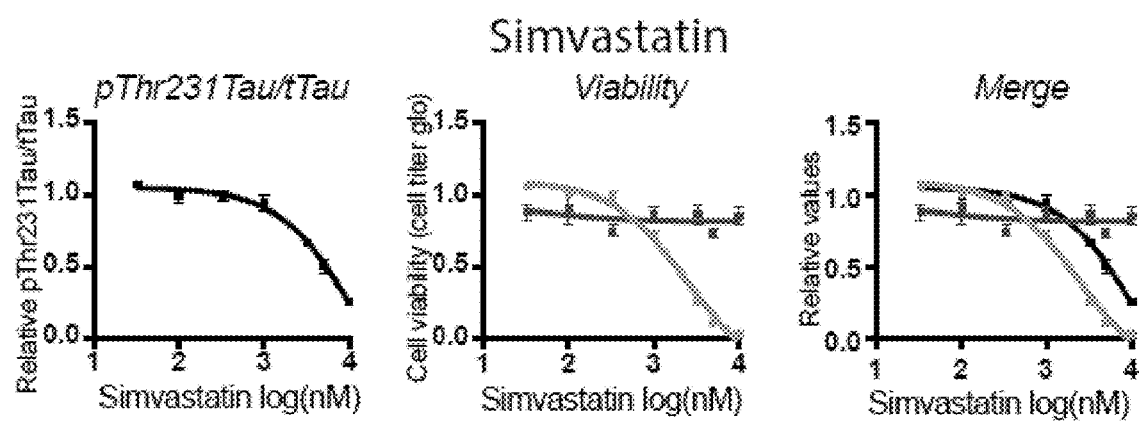
Figure 6D:
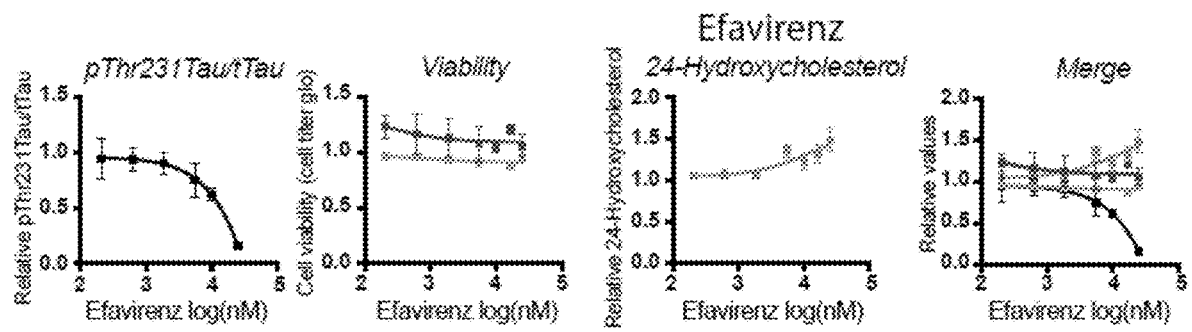

The data indicate that neuronal CE are a potential novel therapeutic target to activate the proteasome and prevent aberrant pTau accumulation in AD. To identify possible adverse effects of candidate CE-lowering strategies on other non-neuronal brain cells, the toxicity of selected compounds was tested on iPSC-derived astrocytes. All iPSC-derived astrocytes displayed radial morphology of astrocytes and expressed the glial marker GFAP, while the neural stem cell marker SOX2 was not expressed (FIG. 6a). Two different drugs which currently have FDA-approval for other indications were concentrated on: statins (to lower cholesterol synthesis) and efavirenz (which activates the neuron-specific enzyme CYP46A1). Already at low concentrations simvastatin and atorvastatin induced major astrocyte cell-death (FIG. 6b-c), whereas efavirenz did not affect astrocyte viability even at high doses (FIG. 6d). 24-hydroxycholesterol was not detected in astrocyte media before or after treatment with efavirenz. Efavirenz increased 24-hydroxycholesterol secretion from APP$^{dp}$ and APP$^{null}$ neurons in a dose dependent manner that correlated well with its effect on pThr231Tau/tTau in these neurons (FIG. 6d). Together these data show that allosteric activation of CYP46A1 is a neuron-specific CE- and pTau lowering treatment with less adverse effects on astrocytes and provides a novel therapeutic approach to reduce pTau accumulation in early AD-neurons.

The examples used AD-patient iPSC-derived neurons in a phenotypic drug screen to identify compounds that reduce aberrant pTau accumulation in FAD neurons (Israel et al., 2012; Moore et al., 2015; Muratore et al., 2014; Ochalek et al., 2017). From a library of >1600 compounds, 42 compounds were identified that reduced pTau levels, including six previously reported modulators of pTau and 36 novel pTau targeting compounds (FIG. 1). This is the first successful example of a screen that identified drugs that lower accumulated pTau in human AD neurons. From the 42 identified compounds, cholesterol-targeting compounds (statins) were selected to study in more detail. Cholesterol metabolism has previously been implicated in AD (Di Paolo and Kim, 2011; Puglielli et al., 2003) and CE, the esterified storage products of cholesterol, accumulate in AD patient brains (Chan et al., 2012) and in APP-transgenic mice (Chan et al., 2012; Tajima et al., 2013; Yang et al., 2014). The data show that reducing CE, through a number of mechanistically different drugs, reduces levels of pTau at multiple phosphorylation epitopes in both FAD, SAD and NDC subject neurons. CE have previously also been shown to regulate APP processing and Aβ generation (Hutter-Paier et al., 2004; Huttunen et al., 2009; Puglielli et al., 2001), and the present data confirmed that CE also regulate Aβ secretion from human iPSC-derived AD patient neurons. Interestingly, it was determined that the effect of CE on Aβ is independent of the effect of CE on pTau (FIGS. 3-4) and that pTau and Aβ are thus co-regulated by CE through independent pathways. Similar co-regulation of Aβ and Tau through independent pathways have recently been shown for ApoE (Wang et al., 2018) and the retromer complex (Young et al., 2018). These findings together with other findings reinforce the notion that common upstream (pathogenic) pathways in SAD, such as CE, can drive increased levels of pTau and Aβ through separate pathways (Small and Duff, 2008), rather than only through a direct linear pathway directly from Aβ to Tau.

Pathways that Mediate the Effect of CE on pTau and Aβ

Figure 6E:
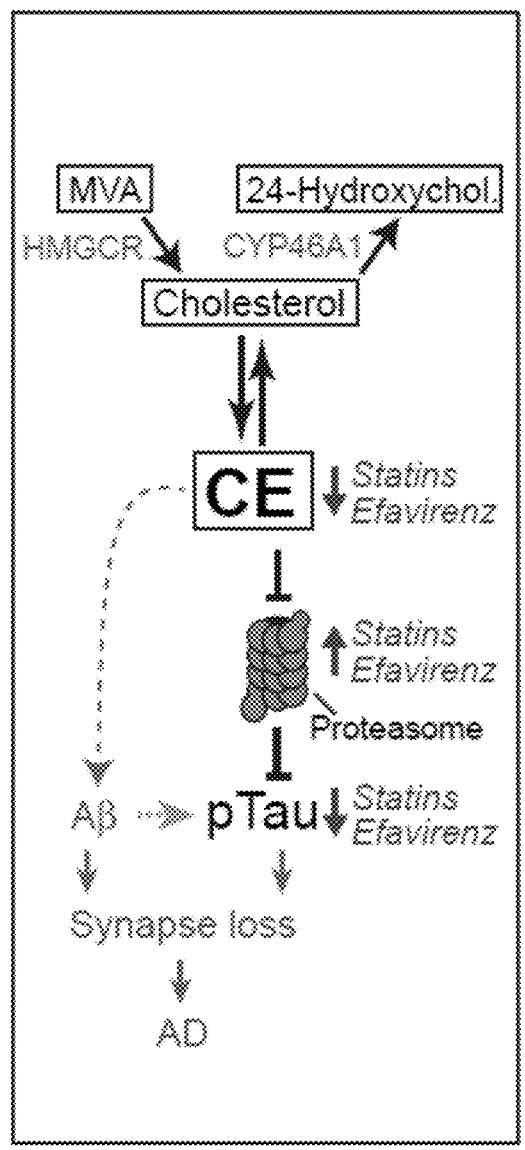

The separate pathway that underlies CE-dependent regulation of pTau and Aβ respectively in early AD neurons was investigated. It was determined that the effect of CE on Aβ is mediated by a cholesterol binding-site in APP, whereas the effect of CE on pTau is mediated by the proteasome. Surprisingly in the present system, no significant differences were observed in free cholesterol levels for the treatments that reduced CE, Aβ and pTau. As also previously observed (Puglielli et al., 2001), this data indicates that CE mediate the effect of cholesterol-targeting drugs on Aβ. The results show that the effect of CE on Aβ is mediated by a domain in APP that has previously been shown to bind cholesterol (Barrett et al., 2012) possibly suggesting that this cholesterol-binding domain can also sense CE. Alternatively, localized reductions in cholesterol in specific domains such as lipid rafts (Ehehalt et al., 2003), specific organelles or localized changes in de-novo synthesized cholesterol under the detection limit of our measurements could mediate the effect of statins on APP processing via the APP-cholesterol binding domain. In regard to CE-dependent regulation of pTau, it was determined that reduction of CE increases the level of proteasomal subunits, overall proteasomal activity and proteasomal degradation of pTau (see model FIG. 6e). This indicates a novel neuronal CE-proteasome-pTau axis that regulates turnover of neuronal pTau. CE-dependent regulation of the proteasome is also relevant for other neurodegenerative diseases in which altered cholesterol-homeostasis and protein aggregation occurs such as Niemann-Pick Type C and Huntington disease (Karasinska and Hayden, 2011). Overall, the data here indicate that CE regulate pTau and Aβ by two separate pathways and suggests that CE is an upstream driver of both Aβ secretion and pTau accumulation.

CE and Alzheimer's Disease.

The present findings provide a mechanistic explanation for how changes in CE, induced by APP mutations or SAD genetic risk variants in APP (Chan et al., 2012; Tajima et al., 2013; Yang et al., 2014) can contribute to Tau pathology. Interestingly, CE production is overactive in human SAD fibroblasts (Pani et al., 2009) and APOE, the major genetic risk factor for SAD, acts as a CE transporter in brain (Liu et al., 2013; Michikawa et al., 2000; Minagawa et al., 2009). The present findings in human iPSC-derived AD neurons indicate that alterations in neuronal CE can drive pTau accumulation and are supported by previous in vivo observations in mouse models showing that statins reduce NFT load in animal models of tauopathy (Boimel et al., 2009) and that genetic inhibition of cholesterol esterification by ACAT1 reduces tauopathy in an AD-mouse model (Shibuya et al., 2015), indicating that the interactions between CE and Tau are conserved in the adult (mouse) brain.

Described herein are several pharmaceutical strategies to reduce CE in early AD-neurons including LXR-target gene mediated cholesterol export, conversion of cholesterol to hydroxycholesterol by CYP46A1 activators and direct inhibition of cholesterol esterification by ACAT inhibitors. In humans, long term statin usage has been shown to correlate with reduced AD incidence in some studies (Shepardson et al., 2011a; 2011b; Zissimopoulos et al., 2017), although the underlying mechanisms have been debated. Statins also reduce p-Tau levels in CSF from AD-patients (Riekse et al., 2006). Here, it is demonstrated that the effects of statins on pTau can be directly mediated by CE, and are not merely a consequence of altered APP processing or peripheral effects of cholesterol-targeting drugs. However, the data do not indicate that statins are the best candidate drugs for targeting Tau accumulation in AD. Statins affect the levels of pTau in human neurons only at relatively high concentrations (FIG. 1) unlikely reached in human brain (Björkhem-Bergman et al., 2011) and have strong adverse effects on human astrocytes at these high concentrations (FIG. 6). The data show that allosteric activators of CYP46A1 can provide a neuron-specific approach to reduce CE and pTau in early AD neurons. Regulation of pTau by CYP46A1 is also conserved in adult (mice) brains where genetic inhibition of CYP46A1 enhances abnormal phosphorylation of Tau (Djelti et al., 2015) and overexpression of CYP46A1 in transgenic Tau mice rescues cognitive decline (Burlot et al., 2015).

CYP46A1 was targeted through allosteric activation by the small molecule efavirenz (Anderson et al., 2016) and it was shown that efavirenz reduces pTau in early human AD-neurons without affecting astrocyte viability. Efavirenz, originally marketed as an HIV-medication (brand name Sustiva), has recently also been shown to reduce amyloid pathology in AD mice (Mast et al., 2017b) indicating that efavirenz can be repurposed for AD. However, when given to HIV patients at high doses, efavirenz has significant adverse effects that include neurotoxicity (Apostolova et al., 2017). Major adverse effects were not observed in mice at lower concentrations of efavirenz that sufficed to alter brain cholesterol metabolism and reduce amyloid pathology indicative of an appropriate therapeutic window (Mast et al., 2017b). Other allosteric activators of CYP46A1 have also recently been identified (Mast et al., 2017a). The in vivo data of CYP46A1 activators on inhibitors of amyloid pathology (Mast et al., 2017b) together with our findings that CYP46A1 activators reduce Tau accumulation in human AD neurons strongly support the use of allosteric activators of CYP46A1 as therapies for AD.

Analysis of 4R Tau-tg Mice Receiving Oral Administration of Compounds.

4R Tau transgenic mice received daily treatments of Efavirenz (0.16 mg/kg), Berberine (25 mg/kg), Simvastatin (30 mg/kg) or vehicle (22.8% DMSO, 40% PEG400 in water) at a volume of 5 ml/kg by oral gavage for 3 months. Following treatment, mice were sacrificed, brains removed and sectioned along the sagittal axis with half flash frozen and half drop fixed in 4% PFA. Fixed brains were sectioned with a vibratome (40 µm) and stained for GFAP, PHF1 (Tau) or Synaptophysin. Sections were imaged with a Leica microscope with a digital camera and analyzed with ImageJ for optical density (GFAP, Synaptophysin) or % area of neuropil (PHF1). Statistics were conducted with Prism6 using ANOVA one way analysis with Tukey-Kramer post hoc analysis.

Figure 7A:
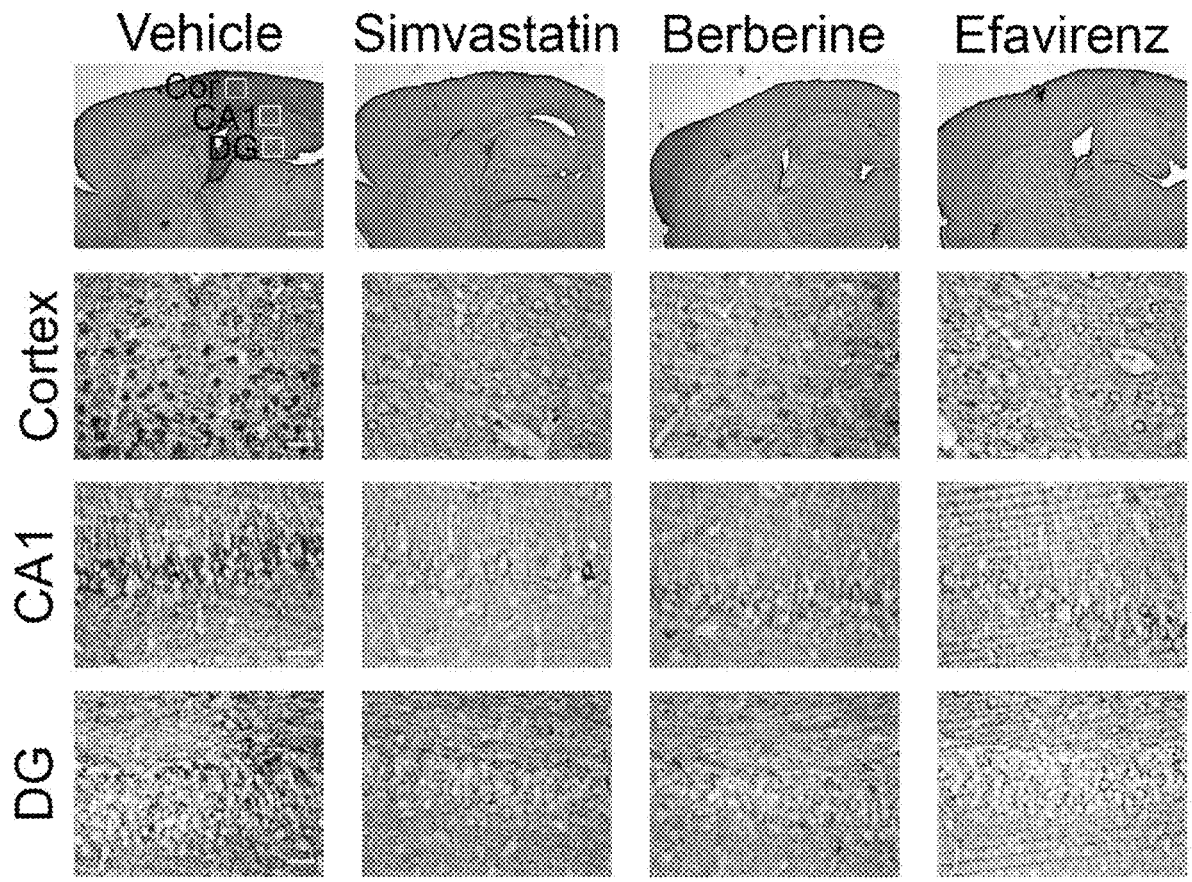
FIGS. 7A-7D show PHF-1 staining of 4RTau-tg mouse sections. 4RTau-tg mice were treated with Simvastatin, Berberine, Efavirenz or Vehicle control for 3 months and then sacrificed, brains removed, sectioned and stained for PHF-1.
Figure 7B:
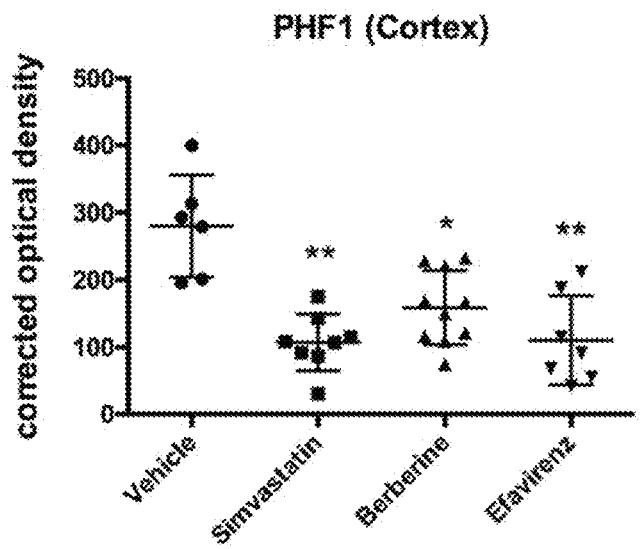
Figure 7C:
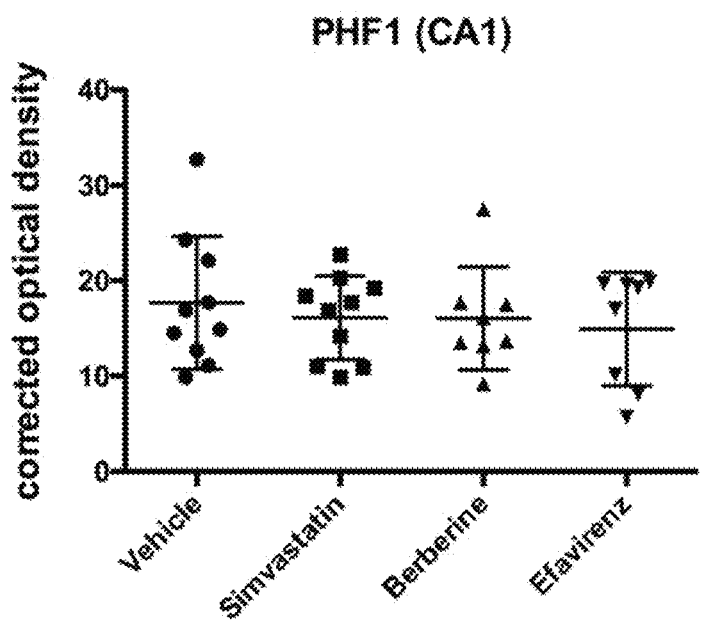
Figure 7D:
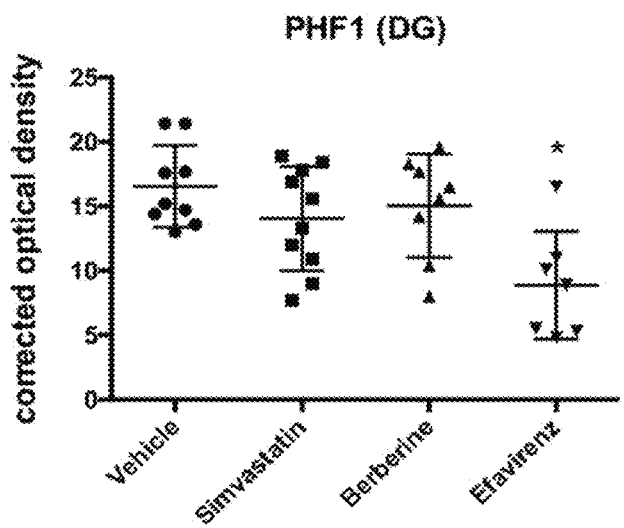

The 4RTau-tg mouse accumulates intra-neuronal Tau in the cortex, hippocampus and striatum as previously shown. Vehicle treated animals showed accumulation of intra-neuronal Tau (PHF-1) in the cortex as well as the CA1 and dentate gyrus granular layers of the hippocampus (FIG. 7A). In addition, granular cells of the of the striatum were positive for Tau (data not shown). Treatment with Simvastatin, Berberine or Efaverinz each significantly reduced the accumulation of Tau in the cortical neurons by over 50% compared to vehicle treated animals (FIGS. 7A and 7B). In addition, Efavirenz significantly reduced the accumulation of Tau in the granular cells of the dentate gyrus compared to vehicle treated animals (FIGS. 7A and 7C). There was no change in the Tau accumulation in the CA1 region of the hippocampus (FIGS. 7A and 7B).

Figure 8A:
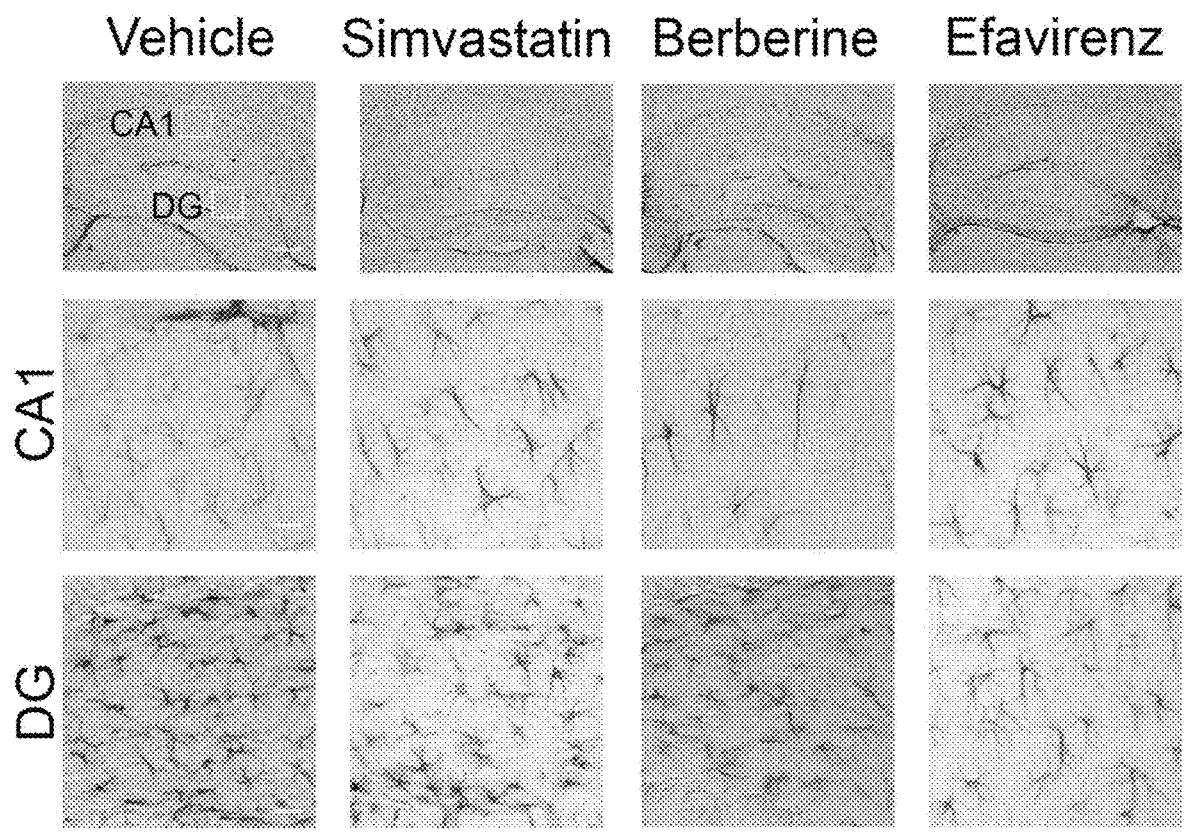
FIGS. 8A-8C show GFAP staining of 4RTau-tg mouse sections. 4RTau-tg mice were treated with Simvastatin, Berberine, Efavirenz or Vehicle control for 3 months and then sacrificed, brains removed, sectioned and stained for GFAP.
Figure 8B:
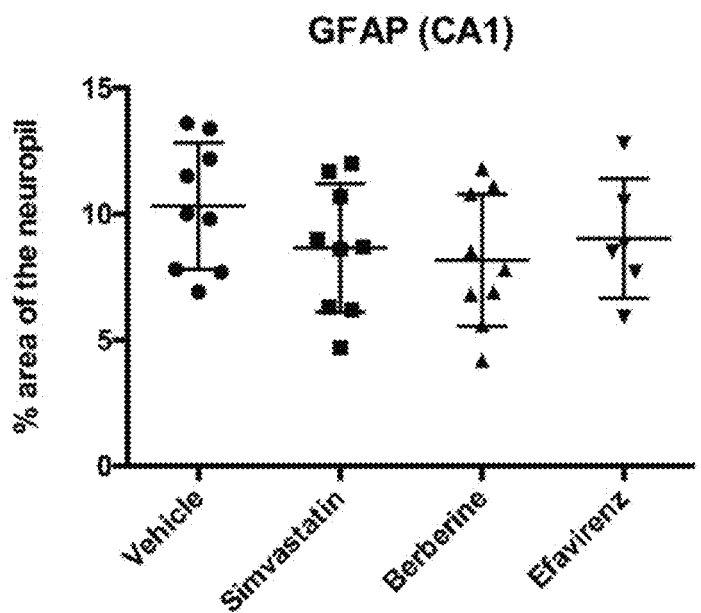
Figure 8C:
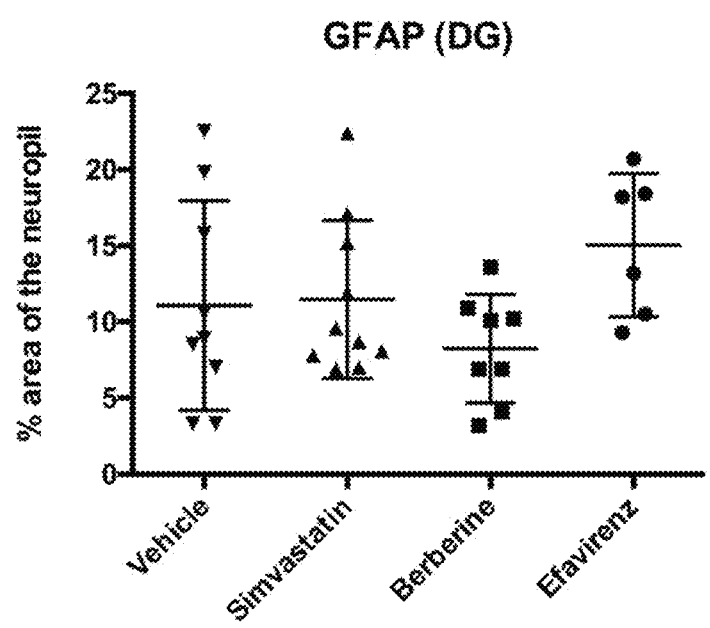
Figure 9A:
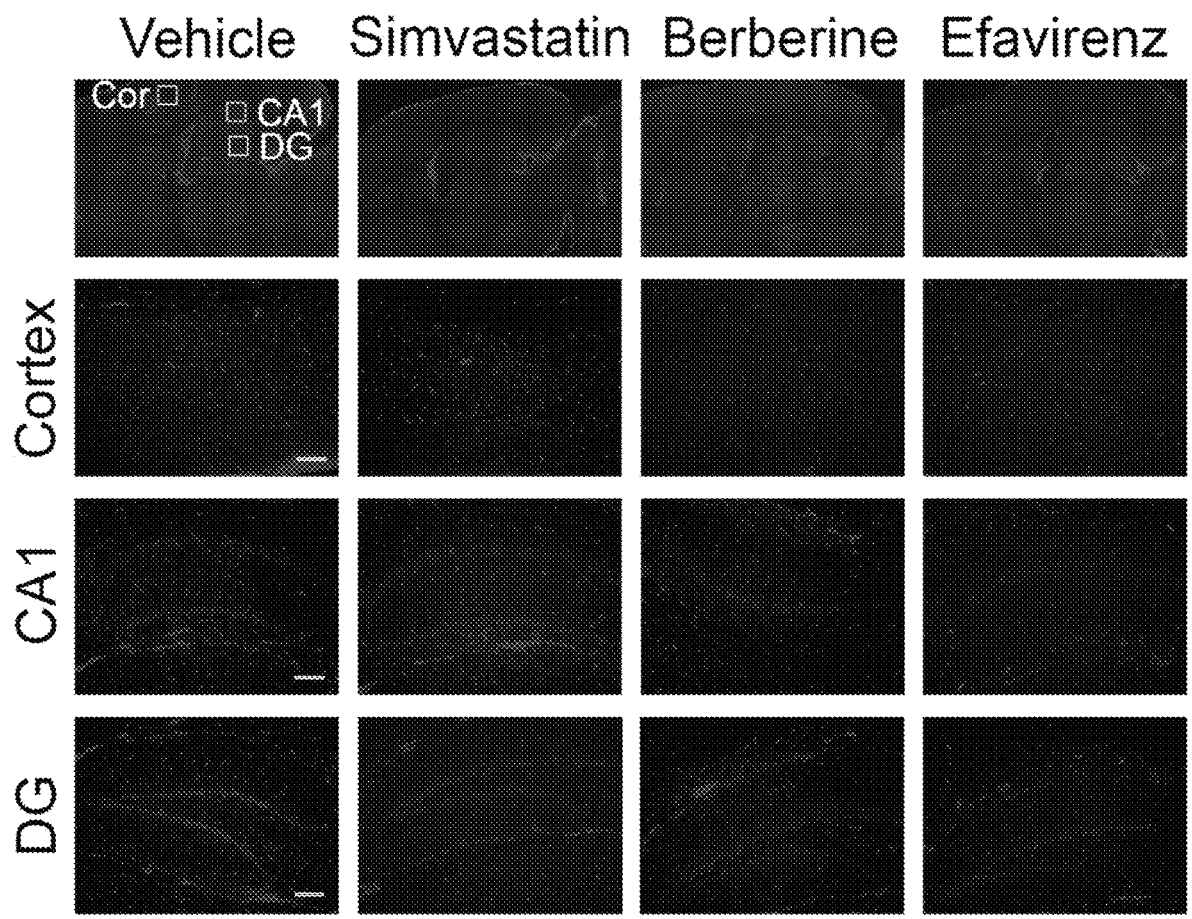
FIGS. 9A-9D show Synaptophysin (SY38) staining of 4RTau-tg mouse sections. 4RTau-tg mice were treated with Simvastatin, Berberine, Efavirenz or Vehicle control for 3 months and then sacrificed, brains removed, sectioned and stained for SY38.
Figure 9B:
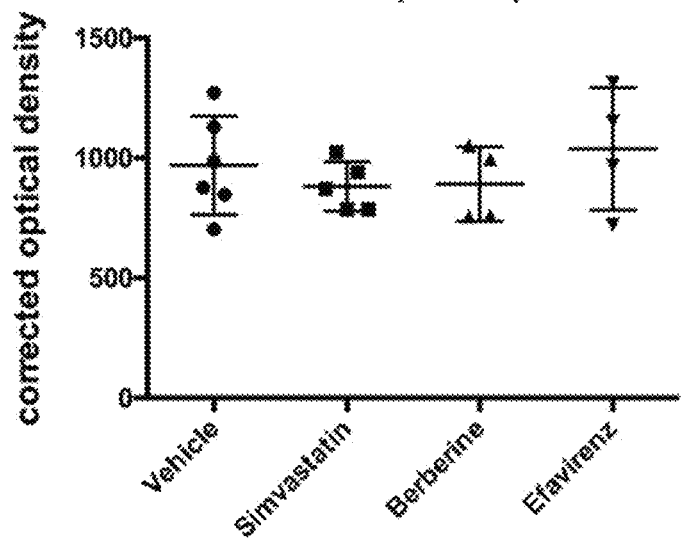
Figure 9C:
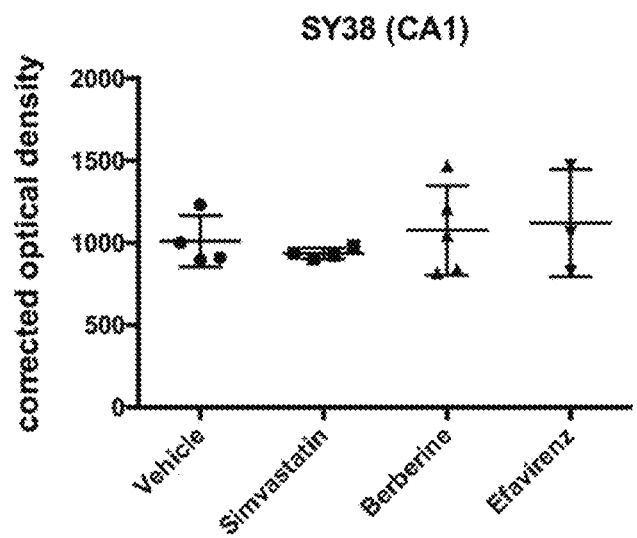
Figure 9D:
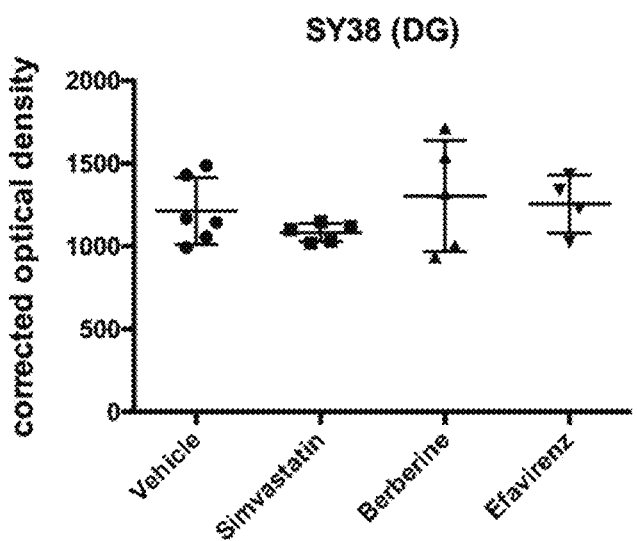

The 4RTau vehicle treated animal stained for GFAP did not show any staining in the cortex, nor did the drug treated animals (data not shown). All animals showed some staining for GFAP, astrocytes, in the hippocampus (FIG. 8A). This was measured in the CA1 and the dentate gyrus neuropil (FIGS. 8B and 8C). No significant differences were observed between the drug treatment groups and the vehicle treated animals.

Synaptophysin, a marker of pre-synaptic terminal, was measured in the cortex and hippocampus (CA1 and dentate gyrus). There was no significant difference between the vehicle treated 4R Tau-tg animals and any of the drug treated tg animals following staining for synaptophysin (FIGS. 9A-9D).

In a prophetic example, the invention provides a method of treatment for tauopathy comprising administering to a human subject in need thereof an effective amount of efavirenz or a derivative thereof. In embodiments, the effective amount is less than 50 mg per day. In embodiments, the effective amount is about 0.01 mg to about 40 mg, or about 0.05 mg to 20 mg, or about 0.1 mg to 5 mg per day, depending upon the condition of the human subject. In embodiments, the tauopathy causes neurofibriliary tangles. In embodiments, the tauopathy is Alzheimer's Disease. In embodiments, the tauopathy is fronto-temporal dementia.

REFERENCES

1. Anderson, K. W., Mast, N., Hudgens, J. W., Lin, J. B., Turko, I. V., Pikuleva, I. A., 2016. Mapping of the Allosteric Site in Cholesterol Hydroxylase CYP46A1 for Efavirenz, a Drug That Stimulates Enzyme Activity. J. Biol. Chem. 291, 11876-11886. doi:10.1074/jbc.M116.723577
2. Apostolova, N., Blas-Garcia, A., Galindo, M. J., Esplugues, J. V., 2017. Efavirenz: What is known about the cellular mechanisms responsible for its adverse effects. European Journal of Pharmacology 812, 163-173. doi: 10.1016/j.ejphar.2017.07.016
3. Arrese, E. L., Saudale, F. Z., Soulages, J. L., 2017. Lipid Droplets as Signaling Platforms Linking Metabolic and Cellular Functions. Lipid Insights 7, LPI.S11128. doi: 10.4137/LPI.S11128
4. Barrett, P. J., Song, Y., Van Horn, W. D., Hustedt, E. J., Schafer, J. M., Hadziselimovic, A., Beel, A. J., Sanders, C. R., 2012. The amyloid precursor protein has a flexible transmembrane domain and binds cholesterol. Science 336, 1168-1171. doi:10.1126/science.1219988
5. Berkers, C. R., van Leeuwen, F. W. B., Groothuis, T. A., Peperzak, V., van Tilburg, E. W., Borst, J., Neefjes, J. J., Ovaa, H., 2007. Profiling proteasome activity in tissue with fluorescent probes. Mol. Pharm. 4, 739-748. doi: 10.1021/mp0700256
6. Björkhem-Bergman, L., Lindh, J. D., Bergman, P., 2011. What is a relevant statin concentration in cell experiments claiming pleiotropic effects? Br J Clin Pharmacol 72, 164-165. doi:10.1111/j.1365-2125.2011.03907.x
7. Boimel, M., Grigoriadis, N., Lourbopoulos, A., Touloumi, O., Rosenmann, D., Abramsky, O., Rosenmann, H., 2009. Statins reduce the neurofibrillary tangle burden in a mouse model of tauopathy. J. Neuropathol. Exp. Neurol. 68, 314-325. doi:10.1097/NEN.0b013e31819ac3cb
8. Brownjohn, P. W., Smith, J., Portelius, E., Serneels, L., Kvartsberg, H., De Strooper, B., Blennow, K., Zetterberg, H., Livesey, F. J., 2017. Phenotypic Screening Identifies Modulators of Amyloid Precursor Protein Processing in Human Stem Cell Models of Alzheimer's Disease. Stem Cell Reports 8, 870-882. doi:10.1016/j.stemcr.2017.02.006
9. Buerger, K., Teipel, S. J., Zinkowski, R., Blennow, K., Arai, H., Engel, R., Hofmann-Kiefer, K., McCulloch, C., Ptok, U., Heun, R., Andreasen, N., DeBernardis, J., Kerkman, D., Moeller, H. J., Davies, P., Hampel, H., 2002. CSF tau protein phosphorylated at threonine 231 correlates with cognitive decline in MCI subjects. Neurology 59, 627-629.
10. Burlot, M.-A., Braudeau, J., Michaelsen-Preusse, K., Potier, B., Ayciriex, S., Varin, J., Gautier, B., Djelti, F., Audrain, M., Dauphinot, L., Fernandez-Gomez, F.-J., Caillierez, R., Laprevote, O., Bièche, I., Auzeil, N., Potier, M.-C., Dutar, P., Korte, M., Buée, L., Blum, D., Cartier, N., 2015. Cholesterol 24-hydroxylase defect is implicated in memory impairments associated with Alzheimer-like Tau pathology. Hum. Mol. Genet. 24, 5965-5976. doi: 10.1093/hmg/ddv268
11. Chan, R. B., Oliveira, T. G., Cortes, E. P., Honig, L. S., Duff, K. E., Small, S. A., Wenk, M. R., Shui, G., Di Paolo, G., 2012. Comparative lipidomic analysis of mouse and human brain with Alzheimer disease. J. Biol. Chem. 287, 2678-2688. doi:10.1074/jbc.M111.274142

12. Choi, S. H., Kim, Y. H., Hebisch, M., Sliwinski, C., Lee, S., D'Avanzo, C., Chen, H., Hooli, B., Asselin, C., Muffat, J., Klee, J. B., Zhang, C., Wainger, B. J., Peitz, M., Kovacs, D. M., Woolf, C. J., Wagner, S. L., Tanzi, R. E., Kim, D. Y., 2014. A three-dimensional human neural cell culture model of Alzheimer's disease. Nature 515, 274-278. doi:10.1038/nature13800

13. D'Antonio, M., Woodruff, G., Nathanson, J. L., D'Antonio-Chronowska, A., Arias, A., Matsui, H., Williams, R., Herrera, C., Reyna, S. M., Yeo, G. W., Goldstein, L. S. B., Panopoulos, A. D., Frazer, K. A., 2017. High-Throughput and Cost-Effective Characterization of Induced Pluripotent Stem Cells. Stem Cell Reports 8, 1101-1111. doi:10.1016/j.stemcr.2017.03.011

14. de Jong, A., Schuurman, K. G., Rodenko, B., Ovaa, H., Berkers, C. R., 2012. Fluorescence-based proteasome activity profiling. Methods Mol. Biol. 803, 183-204. doi:10.1007/978-1-61779-364-6_13

15. Di Paolo, G., Kim, T.-W., 2011. Linking lipids to Alzheimer's disease: cholesterol and beyond. Nat. Rev. Neurosci. 12, 284-296. doi:10.1038/nrn3012

16. Dickey, C. A., Ash, P., Klosak, N., Lee, W. C., Petrucelli, L., Hutton, M., Eckman, C. B., 2006. Pharmacologic reductions of total tau levels; implications for the role of microtubule dynamics in regulating tau expression. Mol Neurodegener 1, 6. doi:10.1186/1750-1326-1-6

17. Djelti, F., Braudeau, J., Hudry, E., Dhenain, M., Varin, J., Bièche, I., Marquer, C., Chali, F., Ayciriex, S., Auzeil, N., Alves, S., Langui, D., Potier, M.-C., Laprevote, O., Vidaud, M., Duyckaerts, C., Miles, R., Aubourg, P., Cartier, N., 2015. CYP46A1 inhibition, brain cholesterol accumulation and neurodegeneration pave the way for Alzheimer's disease. Brain 138, 2383-2398. doi:10.1093/brain/awv166

18. Ehehalt, R., Keller, P., Haass, C., Thiele, C., Simons, K., 2003. Amyloidogenic processing of the Alzheimer beta-amyloid precursor protein depends on lipid rafts. J. Cell Biol. 160, 113-123. doi:10.1083/jcb.200207113

19. Foley, P., 2010. Lipids in Alzheimer's disease: A century-old story. Biochim. Biophys. Acta 1801, 750-753. doi:10.1016/j.bbalip.2010.05.004

20. Fong, L. K., Yang, M. M., Santos Chaves, dos, R., Reyna, S. M., Langness, V. F., Woodruff, G., Roberts, E. A., Young, J. E., Goldstein, L. S. B., 2018. Full-length amyloid precursor protein regulates lipoprotein metabolism and amyloid-β clearance in human astrocytes. J. Biol. Chem. 293, 11341-11357. doi:10.1074/jbc.RA117.000441

21. Giera, M., Plössl, F., Bracher, F., 2007. Fast and easy in vitro screening assay for cholesterol biosynthesis inhibitors in the post-squalene pathway. Steroids 72, 633-642. doi:10.1016/j.steroids.2007.04.005

22. Gore, A., Li, Z., Fung, H.-L., Young, J. E., Agarwal, S., Antosiewicz-Bourget, J., Canto, I., Giorgetti, A., Israel, M. A., Kiskinis, E., Lee, J.-H., Loh, Y.-H., Manos, P. D., Montserrat, N., Panopoulos, A. D., Ruiz, S., Wilbert, M. L., Yu, J., Kirkness, E. F., Izpisua Belmonte, J. C., Rossi, D. J., Thomson, J. A., Eggan, K., Daley, G. Q., Goldstein, L. S. B., Zhang, K., 2011. Somatic coding mutations in human induced pluripotent stem cells. Nature 471, 63-67. doi:10.1038/nature09805

23. Hamilton, L. K., Dufresne, M., Joppé, S. E., Petryszyn, S., Aumont, A., Calon, F., Barnabé-Heider, F., Furtos, A., Parent, M., Chaurand, P., Fernandes, K. J. L., 2015. Aberrant Lipid Metabolism in the Forebrain Niche Suppresses Adult Neural Stem Cell Proliferation in an Animal Model of Alzheimer's Disease. Cell Stem Cell 17, 397-411. doi:10.1016/j.stem.2015.08.001

24. Han, D. H., Na, H.-K., Choi, W. H., Lee, J. H., Kim, Y. K., Won, C., Lee, S.-H., Kim, K. P., Kuret, J., Min, D.-H., Lee, M. J., 2014. Direct cellular delivery of human proteasomes to delay tau aggregation. Nat Commun 5, 5633. doi:10.1038/ncomms6633

25. Hutter-Paier, B., Huttunen, H. J., Puglielli, L., Eckman, C. B., Kim, D. Y., Hofmeister, A., Moir, R. D., Domnitz, S. B., Frosch, M. P., Windisch, M., Kovacs, D. M., 2004. The ACAT inhibitor CP-113,818 markedly reduces amyloid pathology in a mouse model of Alzheimer's disease. Neuron 44, 227-238. doi:10.1016/j.neuron.2004.08.043

26. Huttunen, H. J., Havas, D., Peach, C., Barren, C., Duller, S., Xia, W., Frosch, M. P., Hutter-Paier, B., Windisch, M., Kovacs, D. M., 2010. The acyl-coenzyme A: cholesterol acyltransferase inhibitor CI-1011 reverses diffuse brain amyloid pathology in aged amyloid precursor protein transgenic mice. J. Neuropathol. Exp. Neurol. 69, 777-788. doi:10.1097/NEN.0b013e3181e77ed9

27. Huttunen, H. J., Peach, C., Bhattacharyya, R., Barren, C., Pettingell, W., Hutter-Paier, B., Windisch, M., Berezovska, O., Kovacs, D. M., 2009. Inhibition of acyl-coenzyme A: cholesterol acyl transferase modulates amyloid precursor protein trafficking in the early secretory pathway. FASEB J. 23, 3819-3828. doi:10.1096/fj.09-134999

28. Ikonen, E., 2008. Cellular cholesterol trafficking and compartmentalization. Nat. Rev. Mol. Cell Biol. 9, 125-138. doi:10.1038/nrm2336

29. Israel, M. A., Yuan, S. H., Bardy, C., Reyna, S. M., Mu, Y., Herrera, C., Hefferan, M. P., Van Gorp, S., Nazor, K. L., Boscolo, F. S., Carson, C. T., Laurent, L. C., Marsala, M., Gage, F. H., Remes, A. M., Koo, E. H., Goldstein, L. S. B., 2012. Probing sporadic and familial Alzheimer's disease using induced pluripotent stem cells. Nature 482, 216-220. doi:10.1038/nature10821

30. Kamisuki, S., Mao, Q., Abu-Elheiga, L., Gu, Z., Kugimiya, A., Kwon, Y., Shinohara, T., Kawazoe, Y., Sato, S.-I., Asakura, K., Choo, H.-Y. P., Sakai, J., Wakil, S. J., Uesugi, M., 2009. A small molecule that blocks fat synthesis by inhibiting the activation of SREBP. Chem. Biol. 16, 882-892. doi:10.1016/j.chembiol.2009.07.007

31. Karasinska, J. M., Hayden, M. R., 2011. Cholesterol metabolism in Huntington disease. Nat Rev Neurol 7, 561-572. doi:10.1038/nrneurol.2011.132

32. Keck, S., Nitsch, R., Grune, T., Ullrich, O., 2003. Proteasome inhibition by paired helical filament-tau in brains of patients with Alzheimer's disease. Journal of Neurochemistry 85, 115-122.

33. Keembiyehetty, C. N., Krzeslak, A., Love, D. C., Hanover, J. A., 2011. A lipid-droplet-targeted O-GlcNAcase isoform is a key regulator of the proteasome. J. Cell. Sci. 124, 2851-2860. doi:10.1242/jcs.083287

34. Keller, J. N., Hanni, K. B., Markesbery, W. R., 2001. Impaired Proteasome Function in Alzheimer's Disease. Journal of Neurochemistry 75, 436-439. doi:10.1046/j.1471-4159.2000.0750436.x 35. Kondo, T., Imamura, K., Funayama, M., Tsukita, K., Miyake, M., Ohta, A., Woltjen, K., Nakagawa, M., Asada, T., Arai, T., Kawakatsu, S., Izumi, Y., Kaji, R., Iwata, N., Inoue, H., 2017. iPSC-Based Compound Screening and In Vitro Trials Identify a Synergistic Anti-amyloid β Combination for Alzheimer's Disease. Cell Rep 21, 2304-2312. doi: 10.1016/j.celrep.2017.10.109

36. Lee, H. T., Sliskovic, D. R., Picard, J. A., Roth, B. D., Wierenga, W., Hicks, J. L., Bousley, R. F., Hamelehle, K.

L., Homan, R., Speyer, C., Stanfield, R. L., Krause, B. R., 1996. Inhibitors of Acyl-CoA:Cholesterol O-Acyl Transferase (ACAT) as Hypocholesterolemic Agents. CI-1011: An Acyl Sulfamate with Unique Cholesterol-Lowering Activity in Animals Fed Noncholesterol-Supplemented Diets. Journal of Medicinal Chemistry 39, 5031-5034. doi:10.1021/jm960674d 37. Lee, M. J., Lee, J. H., Rubinsztein, D. C., 2013. Tau degradation: the ubiquitin-proteasome system versus the autophagy-lysosome system. Prog. Neurobiol. 105, 49-59. doi:10.1016/j.pneurobio.2013.03.001

38. Leestemaker, Y., de Jong, A., Witting, K. F., Penning, R., Schuurman, K., Rodenko, B., Zaal, E. A., van de Kooij, B., Laufer, S., Heck, A. J. R., Borst, J., Scheper, W., Berkers, C. R., Ovaa, H., 2017. Proteasome Activation by Small Molecules. Cell Chem Biol 24, 725-736.e7. doi: 10.1016/j.chembiol.2017.05.010

39. Liu, C.-C., Liu, C.-C., Kanekiyo, T., Xu, H., Bu, G., 2013. Apolipoprotein E and Alzheimer disease: risk, mechanisms and therapy. Nat Rev Neurol 9, 106-118. doi:10.1038/nrneurol.2012.263

40. Lokireddy, S., Kukushkin, N. V., Goldberg, A. L., 2015. cAMP-induced phosphorylation of 26S proteasomes on Rpn6/PSMD11 enhances their activity and the degradation of misfolded proteins. Proc. Natl. Acad. Sci. U.S.A. 112, E7176-85. doi:10.1073/pnas.1522332112

41. Luna-Muñoz, J., Chávez-Macías, L., García-Sierra, F., Mena, R., 2007. Earliest stages of tau conformational changes are related to the appearance of a sequence of specific phospho-dependent tau epitopes in Alzheimer's disease. J. Alzheimers Dis. 12, 365-375.

42. Mast, N., Anderson, K. W., Johnson, K. M., Phan, T. T. N., Guengerich, F. P., Pikuleva, I. A., 2017a. In vitro cytochrome P450 46A1 (CYP46A1) activation by neuroactive compounds. J. Biol. Chem. 292, 12934-12946. doi:10.1074/jbc.M117.794909

43. Mast, N., Saadane, A., Valencia-Olvera, A., Constans, J., Maxfield, E., Arakawa, H., Li, Y., Landreth, G., Pikuleva, I. A., 2017b. Cholesterol-metabolizing enzyme cytochrome P450 46A1 as a pharmacologic target for Alzheimer's disease. Neuropharmacology 123, 465-476. doi:10.1016/j.neuropharm.2017.06.026

44. Merrick, S. E., Demoise, D. C., Lee, V. M., 1996. Site-specific dephosphorylation of tau protein at Ser202/Thr205 in response to microtubule depolymerization in cultured human neurons involves protein phosphatase 2A. J. Biol. Chem. 271, 5589-5594.

45. Michikawa, M., Fan, Q. W., Isobe, I., Yanagisawa, K., 2000. Apolipoprotein E exhibits isoform-specific promotion of lipid efflux from astrocytes and neurons in culture. Journal of Neurochemistry 74, 1008-1016.

46. Minagawa, H., Gong, J.-S., Jung, C.-G., Watanabe, A., Lund-Katz, S., Phillips, M. C., Saito, H., Michikawa, M., 2009. Mechanism underlying apolipoprotein E (ApoE) isoform-dependent lipid efflux from neural cells in culture. J. Neurosci. Res. 87, 2498-2508. doi:10.1002/jnr.22073

47. Moore, S., Evans, L. D. B., Andersson, T., Portelius, E., Smith, J., Dias, T. B., Saurat, N., McGlade, A., Kirwan, P., Blennow, K., Hardy, J., Zetterberg, H., Livesey, F. J., 2015. APP metabolism regulates tau proteostasis in human cerebral cortex neurons. Cell Rep 11, 689-696. doi:10.1016/j.celrep.2015.03.068

48. Moutinho, M., Nunes, M. J., Rodrigues, E., 2016. Cholesterol 24-hydroxylase: Brain cholesterol metabolism and beyond. Biochim. Biophys. Acta 1861, 1911-1920. doi:10.1016/j.bbalip.2016.09.011

49. Muratore, C. R., Rice, H. C., Srikanth, P., Callahan, D. G., Shin, T., Benjamin, L. N. P., Walsh, D. M., Selkoe, D. J., Young-Pearse, T. L., 2014. The familial Alzheimer's disease APPV717I mutation alters APP processing and Tau expression in iPSC-derived neurons. Hum. Mol. Genet. 23, 3523-3536. doi:10.1093/hmg/ddu064

50. Müller, C., Binder, U., Bracher, F., Giera, M., 2017. Antifungal drug testing by combining minimal inhibitory concentration testing with target identification by gas chromatography-mass spectrometry. Nat Protoc 12, 947-963. doi: 10.1038/nprot.2017.005

51. Myeku, N., Clelland, C. L., Emrani, S., Kukushkin, N. V., Yu, W. H., Goldberg, A. L., Duff, K. E., 2016. Tau-driven 26S proteasome impairment and cognitive dysfunction can be prevented early in disease by activating cAMP-PKA signaling. Nat. Med. 22, 46-53. doi: 10.1038/nm.4011

52. Naldini, L., Blömer, U., Gallay, P., Ory, D., Mulligan, R., Gage, F. H., Verma, I. M., Trono, D., 1996. In vivo gene delivery and stable transduction of nondividing cells by a lentiviral vector. Science 272, 263-267.

53. Ochalek, A., Mihalik, B., Avci, H. X., Chandrasekaran, A., Téglási, A., Bock, I., Giudice, M. L., Táncos, Z., Molnár, K., László, L., Nielsen, J. E., Holst, B., Freude, K., Hyttel, P., Kobolák, J., Dinnyés, A., 2017. Neurons derived from sporadic Alzheimer's disease iPSCs reveal elevated TAU hyperphosphorylation, increased amyloid levels, and GSK3B activation. Alzheimers Res Ther 9, 90. doi:10.1186/s13195-017-0317-z 54. Pani, A., Dessì, S., Diaz, G., La Colla, P., Abete, C., Mulas, C., Angius, F., Cannas, M. D., Orru, C. D., Cocco, P. L., Mandas, A., Putzu, P., Laurenzana, A., Cellai, C., Costanza, A. M., Bavazzano, A., Mocali, A., Paoletti, F., 2009. Altered cholesterol ester cycle in skin fibroblasts from patients with Alzheimer's disease. J. Alzheimers Dis. 18, 829-841. doi:10.3233/JAD-2009-1193

55. Parrales, A., Ranjan, A., Iyer, S. V., Padhye, S., Weir, S. J., Roy, A., Iwakuma, T., 2016. DNAJA1 controls the fate of misfolded mutant p53 through the mevalonate pathway. Nat. Cell Biol. 18, 1233-1243. doi:10.1038/ncb3427

56. Puglielli, L., Konopka, G., Pack-Chung, E., Ingano, L. A., Berezovska, O., Hyman, B. T., Chang, T. Y., Tanzi, R. E., Kovacs, D. M., 2001. Acyl-coenzyme A: cholesterol acyltransferase modulates the generation of the amyloid beta-peptide. Nat. Cell Biol. 3, 905-912. doi:10.1038/ncb1001-905

57. Puglielli, L., Tanzi, R. E., Kovacs, D. M., 2003. Alzheimer's disease: the cholesterol connection. Nat. Neurosci. 6, 345-351. doi:10.1038/nn0403-345

58. Ramachandran, K. V., Margolis, S. S., 2017. A mammalian nervous-system-specific plasma membrane proteasome complex that modulates neuronal function. Nat. Struct. Mol. Biol. 24, 419-430. doi:10.1038/nsmb.3389

59. Riekse, R. G., Li, G., Petrie, E. C., Leverenz, J. B., Vavrek, D., Vuletic, S., Albers, J. J., Montine, T. J., Lee, V. M.-Y., Lee, M., Seubert, P., Galasko, D., Schellenberg, G. D., Hazzard, W. R., Peskind, E. R., 2006. Effect of statins on Alzheimer's disease biomarkers in cerebrospinal fluid. J. Alzheimers Dis. 10, 399-406.

60. Sharpe, L. J., Cook, E. C. L., Zelcer, N., Brown, A. J., 2014. The UPS and downs of cholesterol homeostasis. Trends Biochem. Sci. 39, 527-535. doi:10.1016/j.tibs.2014.08.008

61. Shepardson, N. E., Shankar, G. M., Selkoe, D. J., 2011a. Cholesterol level and statin use in Alzheimer disease: II. Review of human trials and recommendations. Arch. Neurol. 68, 1385-1392. doi:10.1001/archneurol.2011.242

62. Shepardson, N. E., Shankar, G. M., Selkoe, D. J., 2011b. Cholesterol level and statin use in Alzheimer disease: I. Review of epidemiological and preclinical studies. Arch. Neurol. 68, 1239-1244. doi:10.1001/archneurol.2011.203
63. Shi, Yanhong, Inoue, H., Wu, J. C., Yamanaka, S., 2017. Induced pluripotent stem cell technology: a decade of progress. Nat Rev Drug Discov 16, 115-130. doi:10.1038/nrd.2016.245
64. Shi, Yichen, Kirwan, P., Smith, J., MacLean, G., Orkin, S. H., Livesey, F. J., 2012. A human stem cell model of early Alzheimer's disease pathology in Down syndrome. Sci Transl Med 4, 124ra29-124ra29. doi:10.1126/scitranslmed.3003771
65. Shibuya, Y., Niu, Z., Bryleva, E. Y., Harris, B. T., Murphy, S. R., Kheirollah, A., Bowen, Z. D., Chang, C. C. Y., Chang, T.-Y., 2015. Acyl-coenzyme A:cholesterol acyltransferase 1 blockage enhances autophagy in the neurons of triple transgenic Alzheimer's disease mouse and reduces human P301L-tau content at the presymptomatic stage. Neurobiology of Aging 36, 2248-2259. doi:10.1016/j.neurobiolaging.2015.04.002
66. Small, S. A., Duff, K., 2008. Linking Abeta and tau in late-onset Alzheimer's disease: a dual pathway hypothesis. Neuron 60, 534-542. doi:10.1016/j.neuron.2008.11.007
67. Tajima, Y., Ishikawa, M., Maekawa, K., Murayama, M., Senoo, Y., Nishimaki-Mogami, T., Nakanishi, H., Ikeda, K., Arita, M., Taguchi, R., Okuno, A., Mikawa, R., Niida, S., Takikawa, O., Saito, Y., 2013. Lipidomic analysis of brain tissues and plasma in a mouse model expressing mutated human amyloid precursor protein/tau for Alzheimer's disease. Lipids Health Dis 12, 68. doi:10.1186/1476-511X-12-68
68. Wang, C., Najm, R., Xu, Q., Jeong, D.-E., Walker, D., Balestra, M. E., Yoon, S. Y., Yuan, H., Li, G., Miller, Z. A., Miller, B. L., Malloy, M. J., Huang, Y., 2018. Gain of toxic apolipoprotein E4 effects in human iPSC-derived neurons is ameliorated by a small-molecule structure corrector. Nat. Med. 148, 1204. doi:10.1038/s41591-018-0004-z
69. Xie, H., Litersky, J. M., Hartigan, J. A., Jope, R. S., Johnson, G. V., 1998. The interrelationship between selective tau phosphorylation and microtubule association. Brain Res. 798, 173-183.
70. Yang, D.-S., Stavrides, P., Saito, M., Kumar, A., Rodriguez-Navarro, J. A., Pawlik, M., Huo, C., Walkley, S. U., Saito, M., Cuervo, A. M., Nixon, R. A., 2014. Defective macroautophagic turnover of brain lipids in the TgCRND8 Alzheimer mouse model: prevention by correcting lysosomal proteolytic deficits. Brain 137, 3300-3318. doi:10.1093/brain/awu278
71. Young, J. E., Boulanger-Weill, J., Williams, D. A., Woodruff, G., Buen, F., Revilla, A. C., Herrera, C., Israel, M. A., Yuan, S. H., Edland, S. D., Goldstein, L. S. B., 2015. Elucidating molecular phenotypes caused by the SORL1 Alzheimer's disease genetic risk factor using human induced pluripotent stem cells. Cell Stem Cell 16, 373-385. doi:10.1016/j.stem.2015.02.004
72. Young, J. E., Fong, L. K., Frankowski, H., Petsko, G. A., Small, S. A., Goldstein, L. S. B., 2018. Stabilizing the Retromer Complex in a Human Stem Cell Model of Alzheimer's Disease Reduces TAU Phosphorylation Independently of Amyloid Precursor Protein. Stem Cell Reports 10, 1046-1058. doi:10.1016/j.stemcr.2018.01.031
73. Zissimopoulos, J. M., Barthold, D., Brinton, R. D., Joyce, G., 2017. Sex and Race Differences in the Association Between Statin Use and the Incidence of Alzheimer Disease. JAMA Neurol 74, 225-232. doi:10.1001/jamaneurol.2016.3783

What is claimed is:

1. A method of reducing an accumulation of phosphorylated tau in a human subject, comprising administering to the human subject in need thereof an effective amount of efavirenz, or a derivative thereof, wherein the effective amount is about 5 mg to about 20 mg per day, and wherein reducing the accumulation of phosphorylated tau is effective to treat a tauopathy.

2. The method of claim 1, wherein the tauopathy causes neurofibrillary tangles.

3. The method of claim 1, wherein the tauopathy is Alzheimer's disease.

4. The method of claim 1, wherein the tauopathy is fronto-temporal dementia.

* * * * *